United States Patent
McSheffrey et al.

(10) Patent No.: US 7,891,435 B2
(45) Date of Patent: Feb. 22, 2011

(54) REMOTE INSPECTION OF EMERGENCY EQUIPMENT STATIONS

(75) Inventors: John J. McSheffrey, Hingman, MA (US); John J. McSheffrey, Jr., Needham, MA (US); Brendan T. McSheffrey, Newton, MA (US)

(73) Assignee: en-Gauge, Inc., Rockland, MA (US)

( * ) Notice: Subject to any disclaimer, the term of this patent is extended or adjusted under 35 U.S.C. 154(b) by 730 days.

(21) Appl. No.: 10/614,948

(22) Filed: Jul. 8, 2003

(65) Prior Publication Data

US 2004/0065451 A1    Apr. 8, 2004

Related U.S. Application Data

(63) Continuation-in-part of application No. 10/274,606, filed on Oct. 21, 2002, now Pat. No. 7,188,679, which is a continuation-in-part of application No. 09/832,531, filed on Apr. 11, 2001, now Pat. No. 6,585,055, which is a continuation-in-part of application No. 09/212,121, filed on Dec. 15, 1998, now Pat. No. 6,302,218, which is a continuation of application No. 08/879,445, filed on Jun. 20, 1997, now Pat. No. 5,848,651, which is a continuation-in-part of application No. 08/590,411, filed on Jan. 23, 1996, now Pat. No. 5,775,430, and a continuation-in-part of application No. PCT/US97/01025, filed on Jan. 23, 1997, now abandoned.

(51) Int. Cl.
*A62C 13/76* (2006.01)

(52) U.S. Cl. .............................. 169/75; 169/60; 169/23; 169/30; 169/57; 340/436; 340/539.12; 340/552; 340/611; 607/4; 607/5; 116/67 R; 73/291

(58) Field of Classification Search .................. 169/60, 169/61, 51, 56, 30, 23, 75; 116/2, 4; 340/340, 340/539.1, 435, 436, 904; 607/4–6, 10, 27; 342/27; 367/93
See application file for complete search history.

(56) References Cited

U.S. PATENT DOCUMENTS 922,456 A    5/1909    Casey (Continued)

FOREIGN PATENT DOCUMENTS

DE        3 731 793        3/1989

(Continued)

OTHER PUBLICATIONS

NFPA 10 Standard for Portable Fire Extinguishers, 1998 Edition; Nat'l Fire Protection Assoc., pp. 10.

(Continued)

*Primary Examiner*—Dinh Q Nguyen
(74) *Attorney, Agent, or Firm*—Strategic Patents, P.C.

(57) ABSTRACT

An Apparatus for remote inspection of emergency equipment at one or a system of emergency equipment stations includes, e.g., at each emergency equipment station: a detector for detection of the presence of an obstruction to viewing of or access to the emergency equipment station; and an electronic circuit in communication between the detector and a remote central station for issue of a signal to the remote central station upon detection of the obstruction to viewing of or access to the emergency equipment station.

29 Claims, 13 Drawing Sheets

U.S. PATENT DOCUMENTS

| | | | |
|---|---|---|---|
| 2,670,194 A | | 2/1954 | Hansson |
| 3,145,375 A | | 8/1964 | Webb |
| 3,333,641 A | | 8/1967 | Hansom |
| 3,664,430 A | | 5/1972 | Sitabklhan |
| 3,735,376 A | | 5/1973 | Kermer |
| 3,946,175 A | | 3/1976 | Sitabkhan |
| 4,003,048 A | | 1/1977 | Weise |
| 4,015,250 A | | 3/1977 | Fudge |
| 4,034,697 A | | 7/1977 | Russell |
| 4,051,467 A | | 9/1977 | Galvin |
| 4,100,537 A | | 7/1978 | Carlson |
| 4,101,887 A | | 7/1978 | Osborne |
| 4,119,153 A | * | 10/1978 | Avant .......................... 169/75 |
| 4,125,084 A | | 11/1978 | Salmonsen |
| 4,143,545 A | | 3/1979 | Sitabkhan |
| 4,184,377 A | | 1/1980 | Hubbard |
| 4,246,046 A | | 1/1981 | Lameyer |
| 4,279,155 A | | 7/1981 | Balkanli |
| 4,289,207 A | | 9/1981 | Wernert |
| 4,303,395 A | | 12/1981 | Bower |
| 4,342,988 A | | 8/1982 | Thompson et al. |
| 4,360,802 A | | 11/1982 | Pinto |
| 4,418,336 A | | 11/1983 | Taylor |
| 4,419,658 A | | 12/1983 | Jarosz |
| 4,531,114 A | | 7/1985 | Topol |
| 4,548,274 A | | 10/1985 | Simpson |
| 4,586,383 A | | 5/1986 | Blomquist |
| 4,599,902 A | | 7/1986 | Gray |
| 4,613,851 A | | 9/1986 | Hines |
| 4,697,643 A | | 10/1987 | Sassier |
| 4,805,448 A | | 2/1989 | Armell |
| 4,823,116 A | | 4/1989 | Kitchen, III et al. |
| 4,823,788 A | | 4/1989 | Smith et al. |
| 4,835,522 A | | 5/1989 | Andrejasich et al. |
| 4,866,423 A | | 9/1989 | Anderson |
| 4,887,291 A | | 12/1989 | Stillwell |
| 4,890,677 A | | 1/1990 | Scofield |
| 4,928,255 A | | 5/1990 | Brennecke et al. |
| 4,979,572 A | | 12/1990 | Mikulec |
| 5,123,409 A | | 6/1992 | Sheffield et al. |
| 5,153,567 A | | 10/1992 | Chimento |
| 5,153,722 A | * | 10/1992 | Goedeke et al. ............. 348/159 |
| 5,224,051 A | | 6/1993 | Johnson |
| 5,357,242 A | | 10/1994 | Morgano |
| 5,388,570 A | * | 2/1995 | Wassil ................... 128/200.24 |
| 5,400,246 A | | 3/1995 | Wilson et al. |
| 5,460,228 A | | 10/1995 | Butler |
| 5,475,614 A | | 12/1995 | Tofte et al. |
| 5,486,811 A | | 1/1996 | Wherle |
| 5,534,851 A | | 7/1996 | Russek |
| 5,578,993 A | | 11/1996 | Sitabkhan et al. |
| 5,593,426 A | * | 1/1997 | Morgan et al. ................. 607/5 |
| 5,596,501 A | | 1/1997 | Comer et al. |
| 5,613,778 A | | 3/1997 | Lawson |
| 5,652,393 A | | 7/1997 | Lawson |
| 5,706,273 A | | 1/1998 | Guerreri |
| 5,775,430 A | | 7/1998 | McSheffrey |
| 5,781,108 A | | 7/1998 | Jacob |
| 5,793,280 A | | 8/1998 | Hincher |
| 5,808,541 A | | 9/1998 | Golden |
| 5,848,651 A | | 12/1998 | McSheffrey et al. |
| 5,853,244 A | | 12/1998 | Hoff et al. |
| 5,864,287 A | | 1/1999 | Evans |
| 5,877,426 A | | 3/1999 | Hay |
| 5,936,531 A | | 8/1999 | Powers |
| 5,952,919 A | | 9/1999 | Merrill |
| 6,014,307 A | | 1/2000 | Crimmins |
| 6,114,823 A | | 9/2000 | Doner |
| 6,125,940 A | | 10/2000 | Oram |
| 6,128,576 A | * | 10/2000 | Nishimoto et al. .......... 701/301 |
| 6,141,584 A | * | 10/2000 | Rockwell et al. ................ 607/5 |
| 6,155,160 A | | 12/2000 | Hochbrueckner |
| 6,168,563 B1 | | 1/2001 | Brown |
| 6,240,365 B1 | | 5/2001 | Bunn |
| 6,270,455 B1 | | 8/2001 | Brown |
| 6,289,331 B1 | * | 9/2001 | Pedersen et al. ............... 706/60 |
| 6,301,501 B1 | * | 10/2001 | Cronin et al. ................... 607/5 |
| 6,302,218 B1 | | 10/2001 | McSheffrey et al. |
| 6,311,779 B2 | | 11/2001 | McSheffrey et al. |
| 6,317,042 B1 | | 11/2001 | Engelhorn et al. |
| 6,327,497 B1 | * | 12/2001 | Kirchgeorg et al. ............ 607/3 |
| 6,336,362 B1 | | 1/2002 | Duenas |
| 6,351,689 B1 | | 2/2002 | Carr et al. |
| 6,357,292 B1 | | 3/2002 | Schultz et al. |
| 6,401,713 B1 | | 6/2002 | Hill et al. |
| 6,450,254 B1 | | 9/2002 | Hoyle et al. |
| 6,488,099 B2 | | 12/2002 | McSheffrey et al. |
| 6,496,110 B2 | | 12/2002 | Peterson et al. |
| 6,542,076 B1 | | 4/2003 | Joao |
| 6,585,055 B2 | | 7/2003 | McSheffrey et al. |
| 6,587,049 B1 | | 7/2003 | Thacker |
| 6,598,454 B2 | | 7/2003 | Brazier et al. |
| 6,646,545 B2 | | 11/2003 | Bligh |
| 6,735,473 B2 | * | 5/2004 | Kolder et al. ................... 607/5 |
| 6,853,309 B1 | | 2/2005 | Schröter |
| 6,856,251 B1 | | 2/2005 | Tietsworth et al. |
| 7,271,704 B2 | * | 9/2007 | McSheffrey et al. ... 340/286.05 |
| 7,728,715 B2 | | 6/2010 | Hingham et al. |
| 2001/0052681 A1 | * | 12/2001 | Deavila ................... 280/47.19 |
| 2003/0071736 A1 | | 4/2003 | Brazier et al. |
| 2003/0116329 A1 | | 6/2003 | McSheffrey et al. |
| 2003/0135324 A1 | | 7/2003 | Navab |
| 2003/0189492 A1 | | 10/2003 | Harvie |
| 2004/0017471 A1 | | 1/2004 | Suga et al. |
| 2010/0171624 A1 | | 7/2010 | Mcsheffrey et al. |
| 2010/0245570 A1 | | 9/2010 | Riedel et al. |

FOREIGN PATENT DOCUMENTS

| | | |
|---|---|---|
| FR | 2 340 109 | 9/1977 |
| FR | 2 515 845 | 5/1983 |
| FR | 2 676 931 | 12/1992 |
| WO | WO-81/02484 | 9/1981 |
| WO | WO 81/02484 | 9/1981 |
| WO | WO 94/11853 | 5/1994 |
| WO | WO 01/46780 | 6/2001 |
| WO | WO 01/93220 | 12/2001 |
| WO | WO 03/076765 | 9/2003 |
| WO | WO 03/098908 | 11/2003 |

OTHER PUBLICATIONS

Cole-Panner Brochure, "Exciting New Products for Measuring Flow and Pressure," Canada, received Apr. 23, 1996, 1 page.

Press Release, "Help That comes Too Late Is As Good As No Help At All—The Fire Extinguisher Alarm System Gives Immediate Help", Undated, Invention Technologies, Inc.

Office Action from Canadian Intellectual Property Office dated Dec. 10, 2008.

"PCT/US2004/022019 International Search Report". PCT/US2004/022019 Aug. 7, 2004, all.

, "U.S. Appl. No. 11/856,618, Non-Final Office Action mailed",Sep. 28, 2010, 6 pgs.

, "U.S. Appl. No. 12/716,366, Non-Final Office Action mailed Sep. 15, 2010", , 3 Pgs.

\* cited by examiner

REMOTE INSPECTION OF EMERGENCY EQUIPMENT STATIONS

This application is a continuation-in-part of U.S. application Ser. No. 10/274,606, filed Oct. 21, 2002 now U.S. Pat. No. 7,188,679, which is a continuation-in-part of U.S. application Ser. No. 09/832,531, filed Apr. 11, 2001, now U.S. Pat. No. 6,585,055, issued Jul. 1, 2003, which is a continuation-in-part of U.S. application Ser. No. 09/212,121, filed Dec. 15, 1998, now U.S. Pat. No. 6,302,218, issued Oct. 16, 2001, which is a continuation of U.S. application Ser. No. 08/879,445, filed Jun. 20, 1997, now U.S. Pat. No. 5,848,651, issued Dec. 15, 1998, which is a continuation-in-part of U.S. application Ser. No. 08/590,411, filed Jan. 23, 1996, now U.S. Pat. No. 5,775,430, issued Jul. 7, 1998, and a continuation-in-part of International Application No. PCT/US97/01025, with an International Filing Date of Jan. 23, 1997, now abandoned, the complete disclosures of all of which are incorporated herein by reference.

TECHNICAL FIELD

This invention relates to remote inspection of emergency equipment stations, and, more particularly, to remote inspection of fire extinguisher stations, fire alarm pull stations, emergency lighting stations, defibrillator stations, emergency egress stations, and other similar emergency equipment located at one or a system of emergency equipment stations.

BACKGROUND

Portable fire extinguishers are stationed for use in case of a fire in all manner of environments. Typically, the fire extinguishers are placed in standby condition at a system of fire extinguisher stations found throughout a facility at locations selected for reasonably easy access in a fire emergency. Standards and procedures for periodic inspection of fire extinguishers at fire extinguisher stations are set forth by the National Fire Protection Association (NFPA) in "NFPA 10 Standard for Portable Fire Extinguishers" (1998 Edition), the complete disclosure of which is incorporated herein by reference. In its relevant portion (§4-3.2), NFPA 10 sets forth the elements of the inspection of fire extinguishers and fire extinguisher stations required to take place at regular intervals, e.g., approximately every thirty days, as follows:

4-3.2 Procedures Periodic inspection of fire extinguishers shall include a check of at least the following items:
  (a) Location in designated place
  (b) No obstruction to access or visibility
  (c) Operating instructions on nameplate legible and facing outward
  (d) Safety seals and tamper indicators not broken or missing
  (e) Fullness determined by weighing or "hefting"
  (f) Examination for obvious physical damage, corrosion, leakage, or clogged nozzle
  (g) Pressure gauge reading or indicator in the operable range or position
  (h) Condition of tires, wheels, carriage, hose, and nozzle checked (for wheeled units)
  (i) HMIS ["hazardous materials identification system"] label in place Typically, these inspections are performed manually, and inspection of fire extinguishers at a system of fire extinguisher stations located throughout a facility, e.g., such as a manufacturing plant or an office complex, or throughout an institution, e.g., such as a school campus or a hospital, may occupy one or more employees on a full time basis. Procedures for more frequent inspections are generally considered cost prohibitive, even where it is recognized that a problem of numbers of missing or non-functioning fire extinguishers may not be addressed for days or even weeks at a time, even where manpower may otherwise be available.

SUMMARY

According to one aspect of the invention, an apparatus for remote inspection of emergency equipment in installed positions at one or a system of emergency equipment stations comprises: a detector located at a emergency equipment station for detection of the presence of an obstruction to viewing of or access to the emergency equipment station; and an electronic circuit in communication between the detector and a remote central station for issue of a signal to the remote central station upon detection of the obstruction to viewing of or access to the emergency equipment station.

Preferred embodiments of this aspect of the invention may include one or more of the following additional features. The emergency equipment station may include a fire extinguisher station. The emergency equipment station may include a fire alarm pull station. The emergency equipment station may include a defibrillator station with a portable defibrillator. The emergency equipment station may include an emergency lighting station and the obstruction to viewing may act as an obstruction to operation for illumination. The detector may initiate a signal from the electronic circuit to the remote central station upon detection of the obstruction. The signal may include a wireless signal. The obstruction may be disposed within a range of about 6 inches to about 10 feet from the emergency equipment station. The detector may initiate a signal from the electronic circuit to another emergency equipment station upon detection of the obstruction. The signal to another emergency equipment station may include a wireless signal. The detector may comprise a proximity sensor. The proximity sensor may comprise an acoustic signal transmitter and an acoustic signal detector. The proximity sensor may comprise an ultrasonic transducer. The proximity sensor may comprise an electromagnetic signal detector. The proximity sensor may comprise an electromagnetic signal transmitter and an electromagnetic signal detector. The proximity sensor may comprise an optical signal transmitter and an optical signal detector. The proximity sensor may comprise an infrared signal transmitter and an infrared signal detector. The electronic circuit may be further adapted to issue a signal to the remote central station and to receive another signal from the remote central station. The issued signal to the remote central station and received signal from the remote central station may include a wireless signal. The electronic circuit may further comprise a wireless signal transmitter for transmitting a wireless signal to the remote central station. The electronic circuit may further comprise a wireless signal receiver for receiving a wireless signal from the remote central station. The electronic circuit may further comprise a receiver for receiving a signal from another emergency equipment station. The electronic circuit may further comprise a receiver for receiving a wireless signal from another emergency equipment station. The electronic circuit may further comprise a transmitter for transmitting a signal to another emergency equipment station. The electronic circuit may further comprise a transmitter for transmitting a wireless signal to another emergency equipment station. The emergency equipment station may include an emergency egress station. The detector may be included in a housing separated from the emergency equipment.

The invention thus provides an apparatus for remote inspection of emergency equipment stations such as fire extinguisher stations, fire alarm pull stations, defibrillator stations, emergency lighting stations, etc., permitting at least more frequent, and, if desired, continuous, monitoring and inspection of the emergency equipment located at the emergency equipment stations. By remotely inspecting and/or monitoring the emergency equipment stations, the frequency with which safety personnel must physically inspect each station is markedly reduced, which correspondingly reduces inspection time and cost. Furthermore, by monitoring for obstructions to the visibility of and access to the emergency equipment stations, safety personnel are alerted to the potential hazard that an employee or passerby might be unable to locate, or to gain access to, the emergency equipment station during an emergency such as a fire or other life-threatening event.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
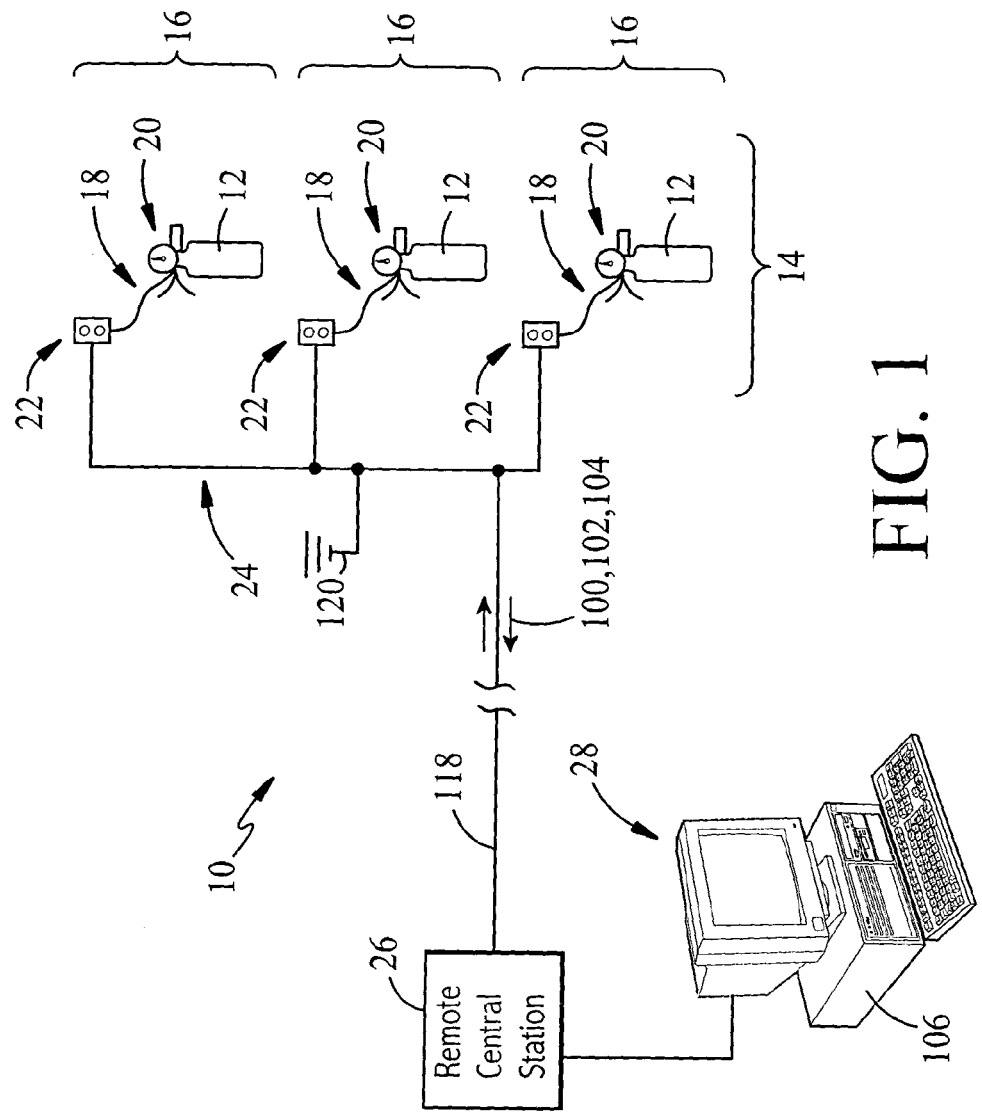
FIG. 1 is a somewhat diagrammatic view of an apparatus of the invention for remote inspection of fire extinguishers at a system of fire extinguisher stations.

Referring to FIG. 1, in one embodiment, an apparatus 10 of the invention for remote inspection of portable fire extinguishers 12 installed at one or a system 14 of fire extinguisher stations 16 includes means 18 for detecting lack of presence of a fire extinguisher 12 in its installed position at a fire extinguisher station 16, means 20 for detecting out-of-range pressure of the contents of a fire extinguisher 12 at a fire extinguisher station 16, means 22 for detecting an obstruction to viewing of or access to a fire extinguisher station 16, and means 24 for transmission of inspection report information for each of the fire extinguisher stations 16 to a remote central station 26. The apparatus 10 may further include means 28 for maintaining a record of inspection report information.

Figure 2:
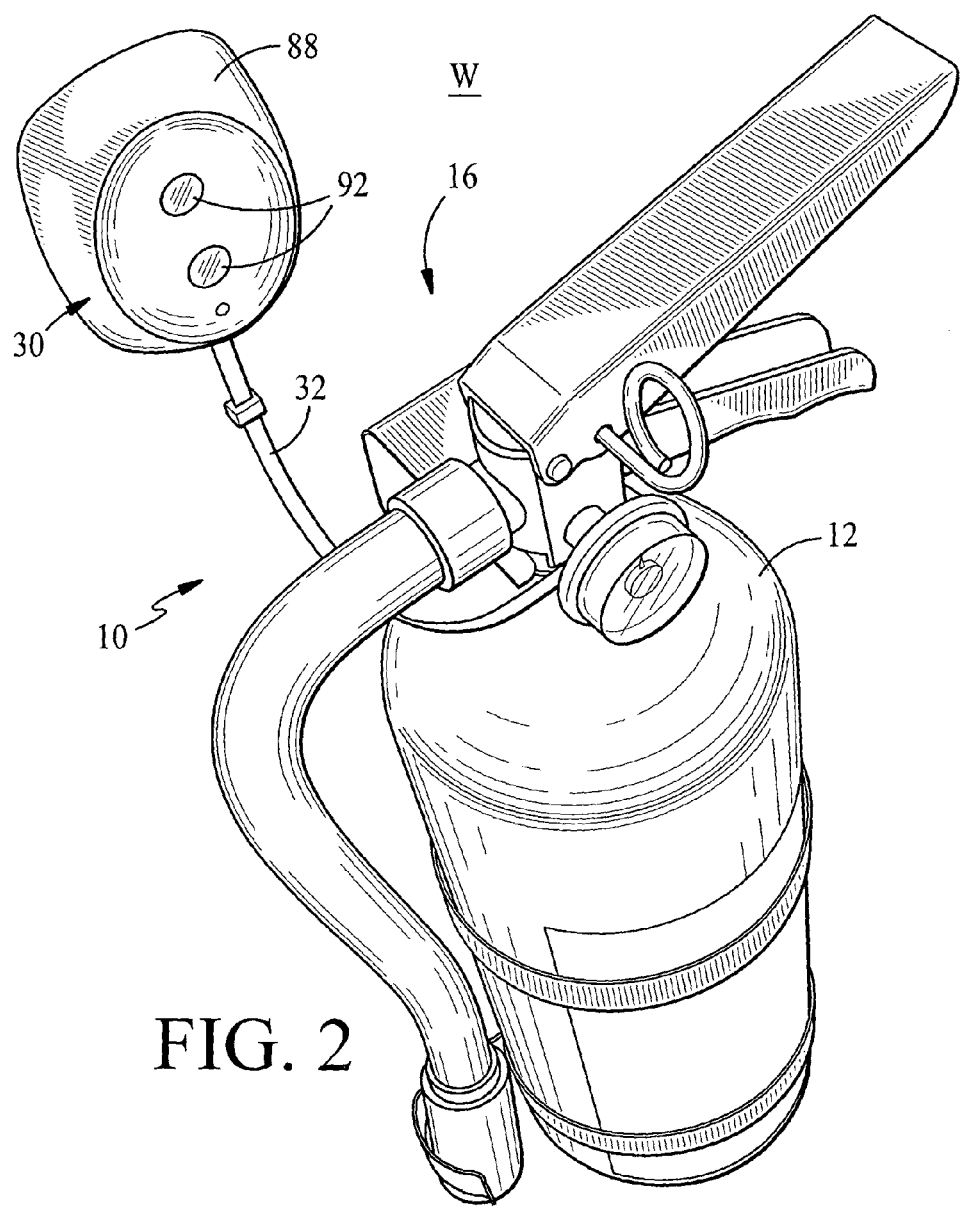
FIG. 2 is a perspective view of a fire extinguisher mounted at a fire extinguisher station for remote inspection according to the invention.
Figure 3:
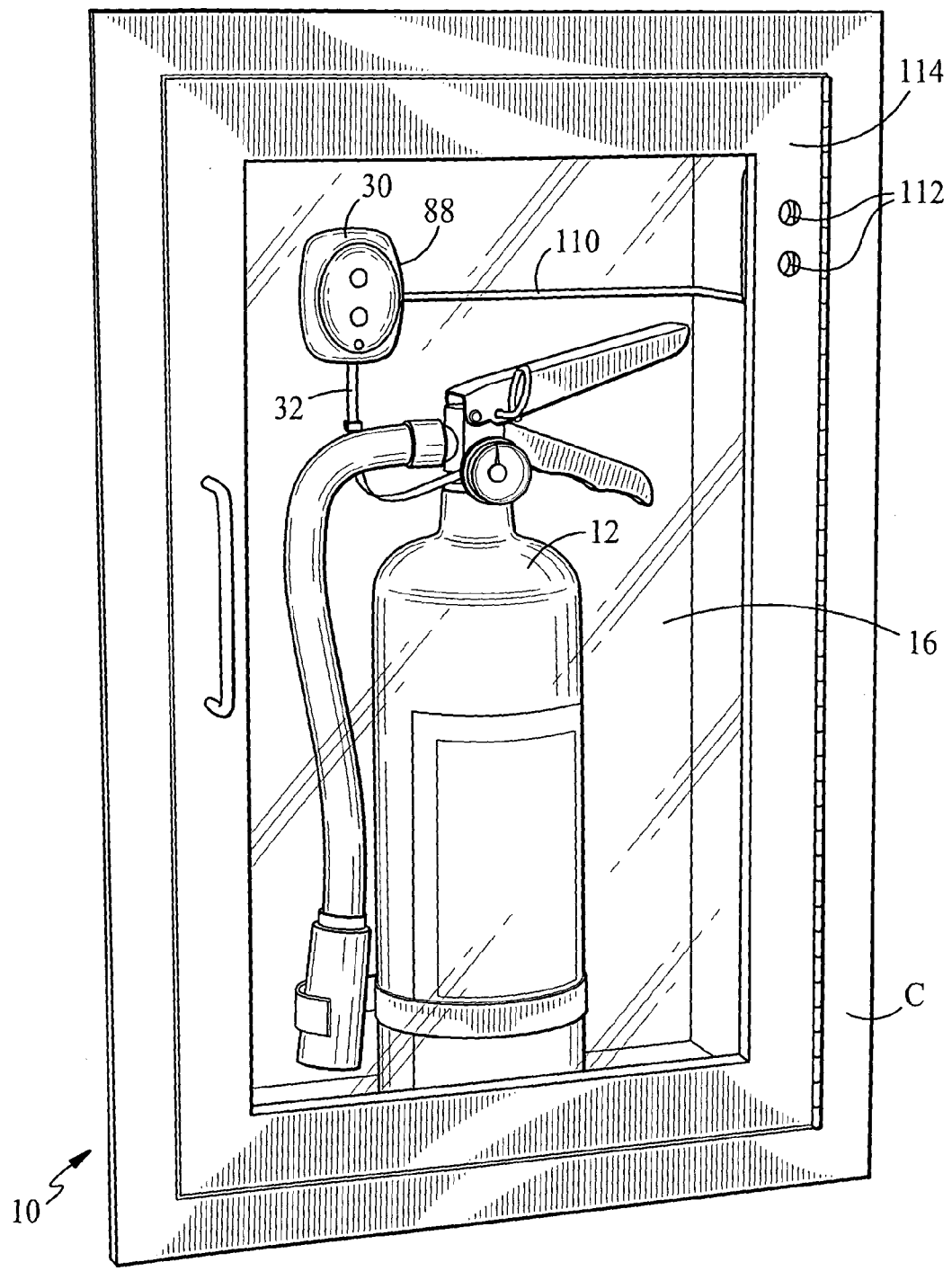
FIG. 3 is a perspective view of a fire extinguisher mounted at another fire extinguisher station for remote inspection according to the invention.

As an example of a remote inspection apparatus 10 of the invention, in FIG. 2, a portable fire extinguisher 12 is shown mounted to a wall, post, or other support surface, W, at a fire extinguisher station 16 in a system of fire extinguisher stations 14, and in FIG. 3, another portable fire extinguisher 12 is shown mounted within a wall box or cabinet, C, at another fire extinguisher station 16 in the system of fire extinguisher stations 14. In this embodiment, the fire extinguisher 12 at each fire extinguisher station 16 is releasably connected to a docking station 30 by an electronics and communications tether 32 to provide a releasable engagement for electronics and/or communications connection between the docking station 30 and the portable fire extinguisher(s) 12 at each of the fire extinguisher stations 16. Typically signals issued from or to the fire extinguisher 12 are transmitted over the electronics and communication tether 32. For example, a signal, initiated by one or more Hall Effect sensors included in the fire extinguisher 12, which is indicative of out-of-range (low or high) pressure of the fire extinguishing material contained within the tank volume, is transmitted from the fire extinguisher 12 across the tether 32 to the docking station 30 and then to the remote central station 26.

In the embodiment shown in FIG. 2, the docking station 30 is fixedly mounted to the wall, W, at a predetermined position spaced generally above the fire extinguisher 12. The docking station 30 consists of a housing 88 containing a sonar module 90 (shown in FIG. 4b) and defining spaced apertures or windows 92 through which the module 90 emits and receives ultrasonic signals. In the embodiment of FIG. 3, where the docking station 30 is disposed with a wall cabinet, C, the sonar module 90 is connected, e.g., by cable 110, to apertures or windows 112 in the outer surface of the cabinet door 114 for emitting and receiving the ultrasonic signals. Also, disposed within the docking station housing 88 is an electronic and communications circuit 94, as described more fully below with reference to FIG. 4. Extending generally from the base of the docketing station housing 88 is the electronics and communications tether 32 received by a connector in communication with a value that monitors the internal content pressure of the fire extinguisher. The length of the tether 32, and the tenacity of engagement of the connection between the connector and the tether, are preferably selected so that any significant movement of the fire extinguisher 12 relative to its installed position, i.e., the position in which it is placed at installation by a fire extinguisher professional, whether removal, or, in a preferred embodiment, merely upon rotation with movement in excess of a predetermined threshold value, will result in dislodgement of the tether 32 from the connector, initiating a signal to the remote central station 26, as discussed more fully below. The docking station 30 may be powered by alternating current, e.g., by a hardwire connection into a facility's electrical supply, or it may be powered by direct current, e.g., by a battery within the docking station housing 88. If powered by alternating current, an auxiliary power supply, e.g., in the form of a battery, may be provided in case of power outage.

Figure 4:
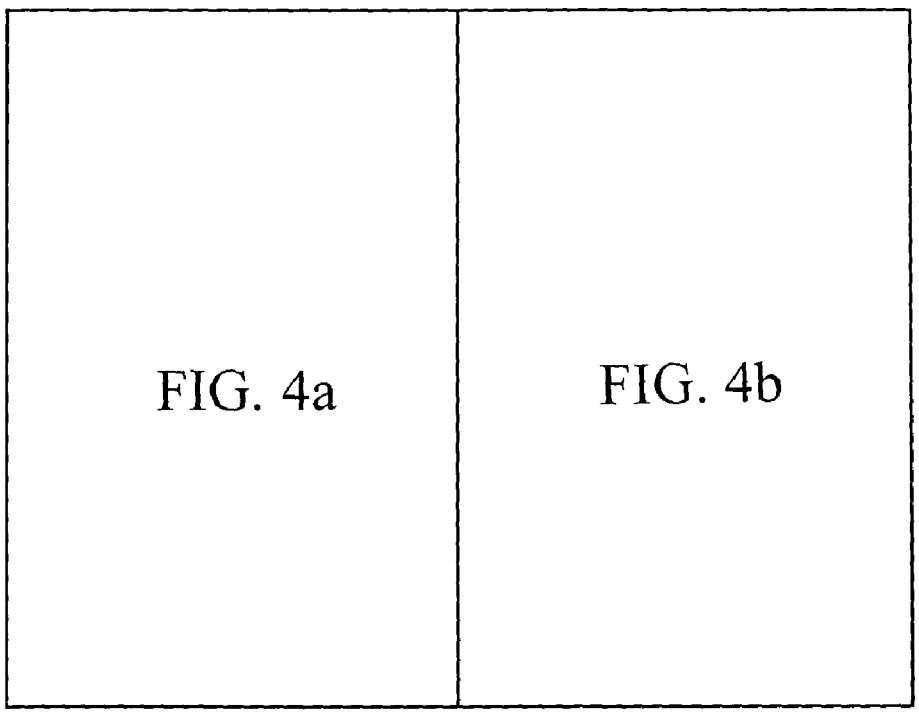
FIG. 4 is a block diagram of the electronics and communications circuit for one embodiment of a remote inspection apparatus of the invention that are depicted in FIGS. 4a and 4b.
Figure 4A:
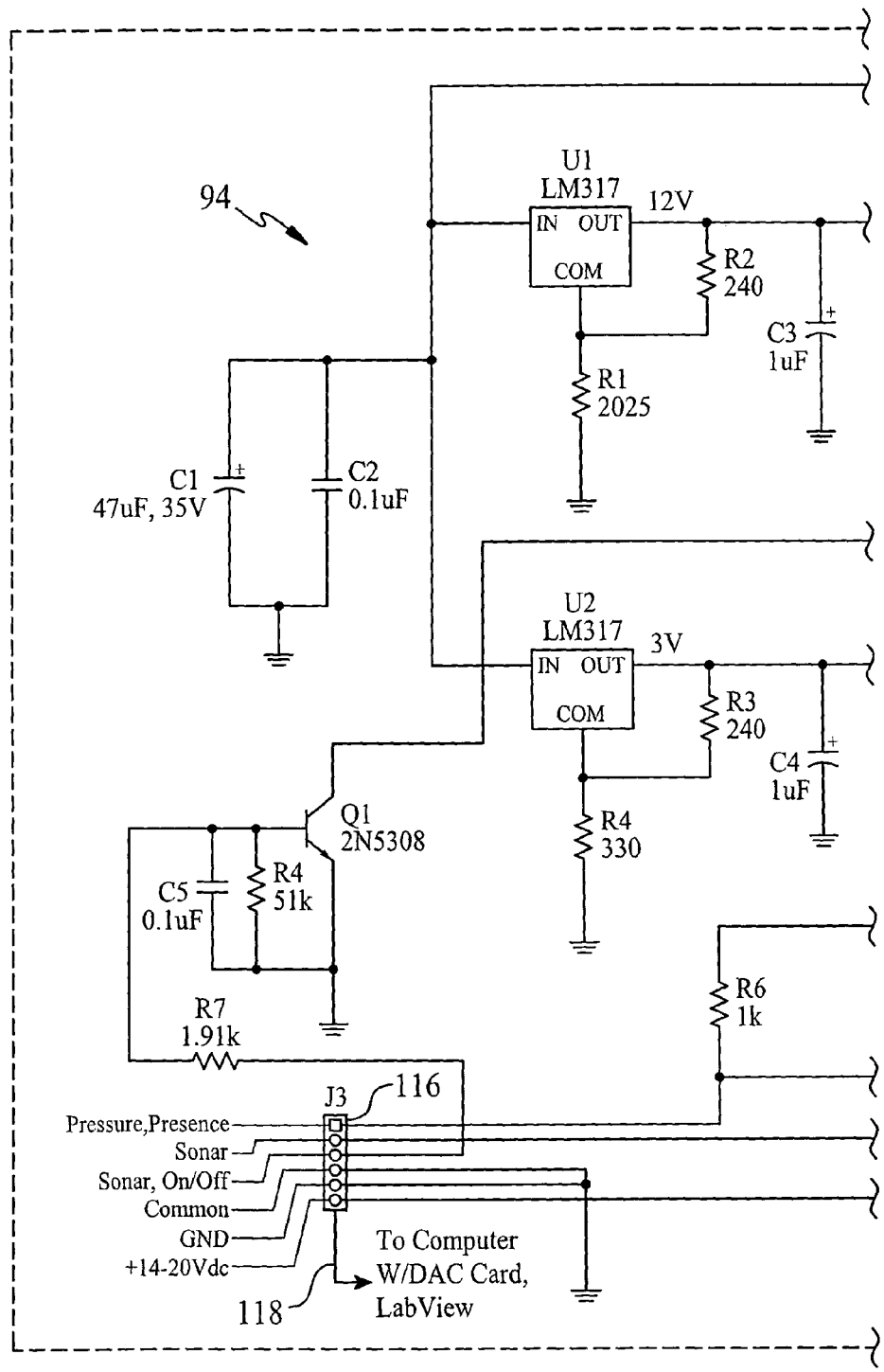
Figure 4B:
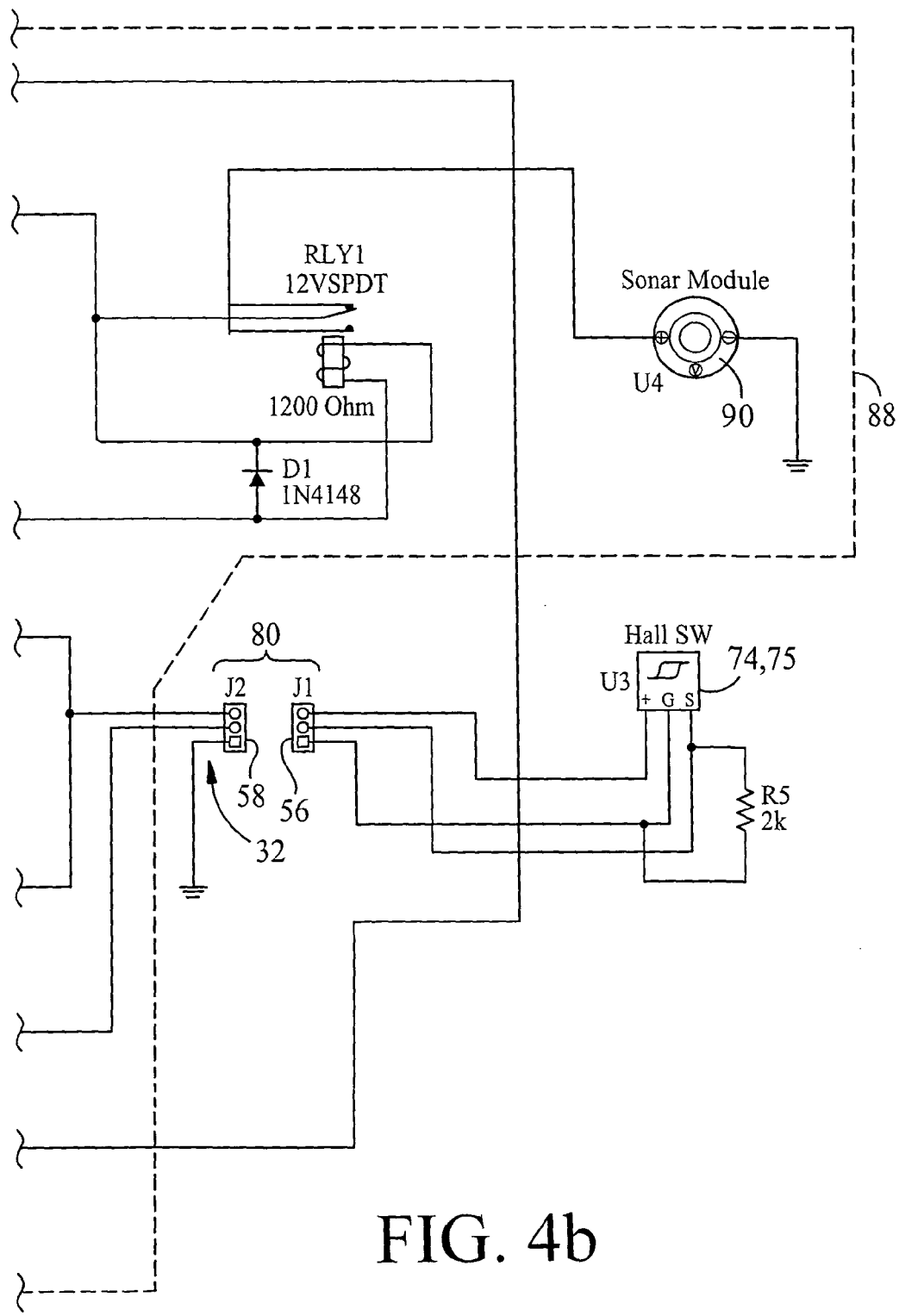

Referring now to FIG. 4, the remote inspection apparatus 10 includes an electronics and communications circuit 94, e.g., disposed primarily within the docking station 30, for initiating signals to the remote central station 26 upon detection of predetermined internal and/or predetermined external conditions. For example, referring again to FIG. 1, in the preferred embodiment, the circuit 94 issues a signal 100 or a signal 102 upon detection of a predetermined external condition, e.g., lack of presence of the fire extinguisher 12 at its installed position at the fire extinguisher station 16, when the fire extinguisher 12 is removed from, or moved within, the fire extinguisher station, thereby disengaging the tether 32 from the connection with the fire extinguisher 12, and disrupting the closed connection 80 (signal 100), or an obstruction to viewing of or access to a fire extinguisher station 16 (signal 102). The circuit 94 also issues a signal 104 upon detection of a predetermined internal condition, e.g., existence of an out-of-range, e.g., low, pressure condition of the fire extinguishing material contained within the tank of the fire extinguisher 12.

According to one embodiment, the signals 100, 104 are communicated via an electronics and communications connection 80 of a male connector element 58 of the tether 32 with a female socket 56 of the fire extinguisher 12 to electronics and communications circuit 94 within docking station 30. The signal 100 indicating lack of presence of the fire extinguisher 12 in its installed position at the fire extinguisher station 16 and signal 104 indicating that pressure of the fire extinguishing material in the tank of the fire extinguisher 12 is below a predetermined minimum pressure level, e.g., indicative of a discharge, leak or other malfunction (or, in an embodiment with a pair of Hall Effect sensors 74, 75, above a predetermined maximum pressure level) are received by a connection and termination strip process control board 116 and transmitted via hardwire connection 118 to the remote central station 26. In this embodiment, the tether 32 includes a two wire connection in normally closed state, signaling the presence of the fire extinguisher 12, and a two wire connection in normally open state that signals that pressure in the fire extinguisher tank is above the predetermined minimum level. The signals are received and transmitted over the hardwire connection 118. However, it is contemplated that, in other embodiments, signals 100, 102, 104 may be communicated, e.g., via radio frequency (RF), or other, wireless communication circuitry via antenna 120 (FIG. 1) to an RF monitoring system receiver, e.g., at the remote central station 26, or simultaneously, via both hardwire and wireless, to a remote central station 26, or other monitoring station. As mentioned above, it is also contemplated that the remote inspection apparatus 10 may be powered by alternating current, e.g., by a hardwire connection to the facility electric supply system or by direct current, e.g. by battery, or by both, with the battery provided as auxiliary power in case the primary electrical service is disrupted.

Figure 5:
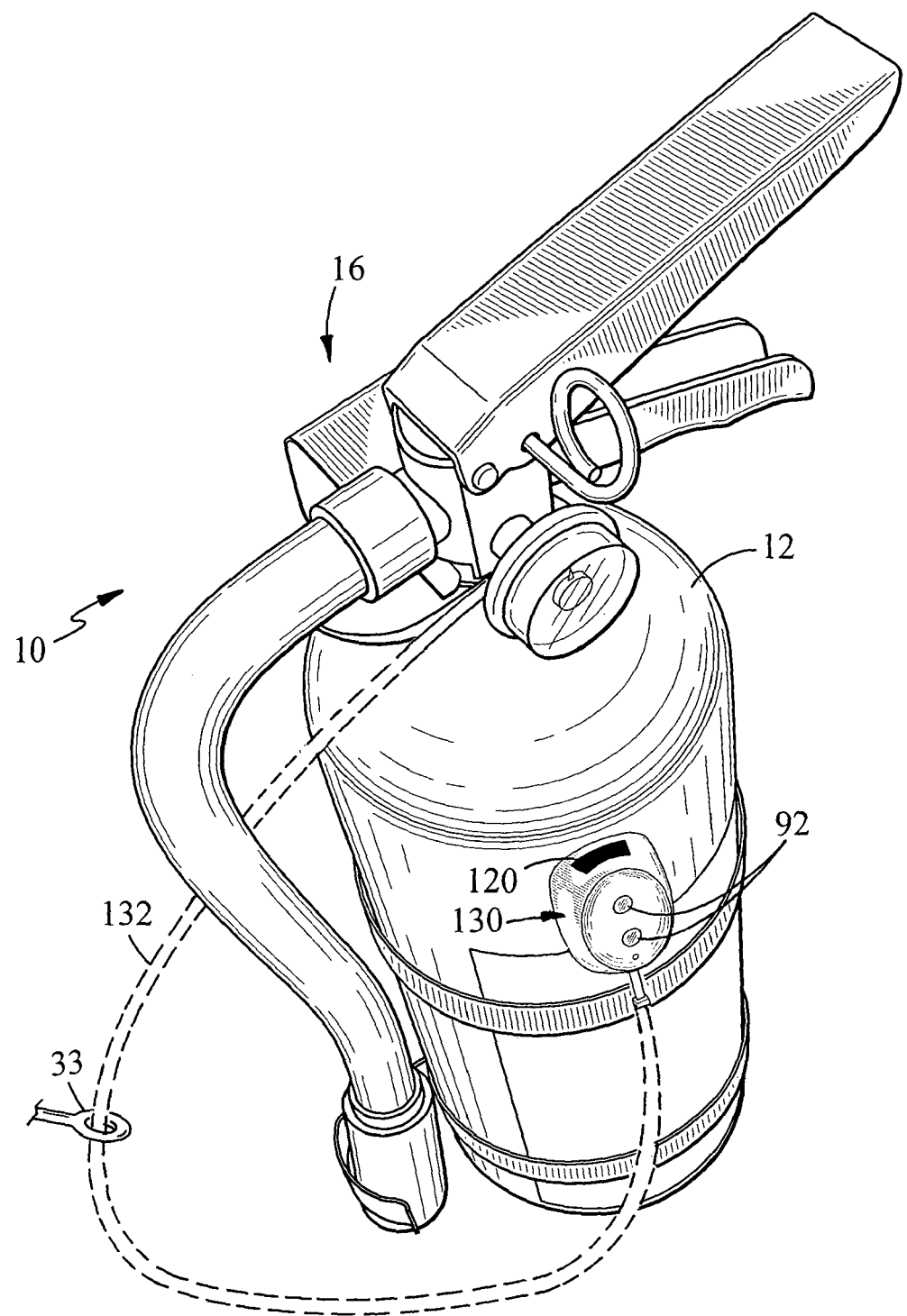
FIG. 5 is a perspective view of elements of another embodiment of the apparatus of the invention for remote inspection of a fire extinguisher station with components of a docking station mounted to the fire extinguisher for communication with a remote central station by wireless signal.

Referring to FIG. 5, in another embodiment, components of docking station 30, as described above, may instead be mounted to the fire extinguisher 12, e.g., within a housing 130, thereby allowing the fire extinguisher to be located, if desired, without wall mounting or enclosure. In the embodiment shown, housing 130 contains the sonar module 90 and defines the apertures or windows 92 for detecting obstructions as previously mentioned. Electronic and communications circuitry 94 is also disposed within the housing 130, for communication of signals, e.g., wireless signals, between the fire extinguisher station 16 and the remote central station 26.

An electronics and communication tether 132 may extend between connections to the housing 130 and the fire extinguisher 12, as indicated in dashed line, e.g., engaged through an aperture of an I-bolt 33 anchored into a wall W, such that any significant movement of the fire extinguisher 12 relative to its position at rest, in excess of a predetermined threshold value, results in disengagement of the tether 132 from connection with the extinguisher 12, thereby to initiate a wireless signal to the remote central station 26 (FIG. 1). In another embodiment (not shown), a tether or leash, e.g. in the form of a cord, wire, rope or the like, may extend from a first end secured, e.g., to a wall, to engagement of its second end in a socket defined, e.g., by the housing 130, whereby dislodgement of the tether or leash from the socket initiates a wireless signal.

Wireless communication circuitry and antenna 120 (FIG. 1) are located within the housing 130 to communicate by wireless signal between the fire extinguisher 12 and the previously mentioned RF monitoring system receiver, e.g., at the remote central station 26. Signals 100, 102 are communicated by wireless signal between the remote central station 26 (FIG. 1) and the fire extinguisher station 16 upon detecting the previously mentioned predetermined external conditions. Signals, such as signal 104, are also communicated by wireless signal upon detection of the previously mentioned predetermined internal conditions. In this manner, a system of fire extinguishers, distributed over a considerable area, are maintained in wireless communication with the remote central station 26.

Figure 6:
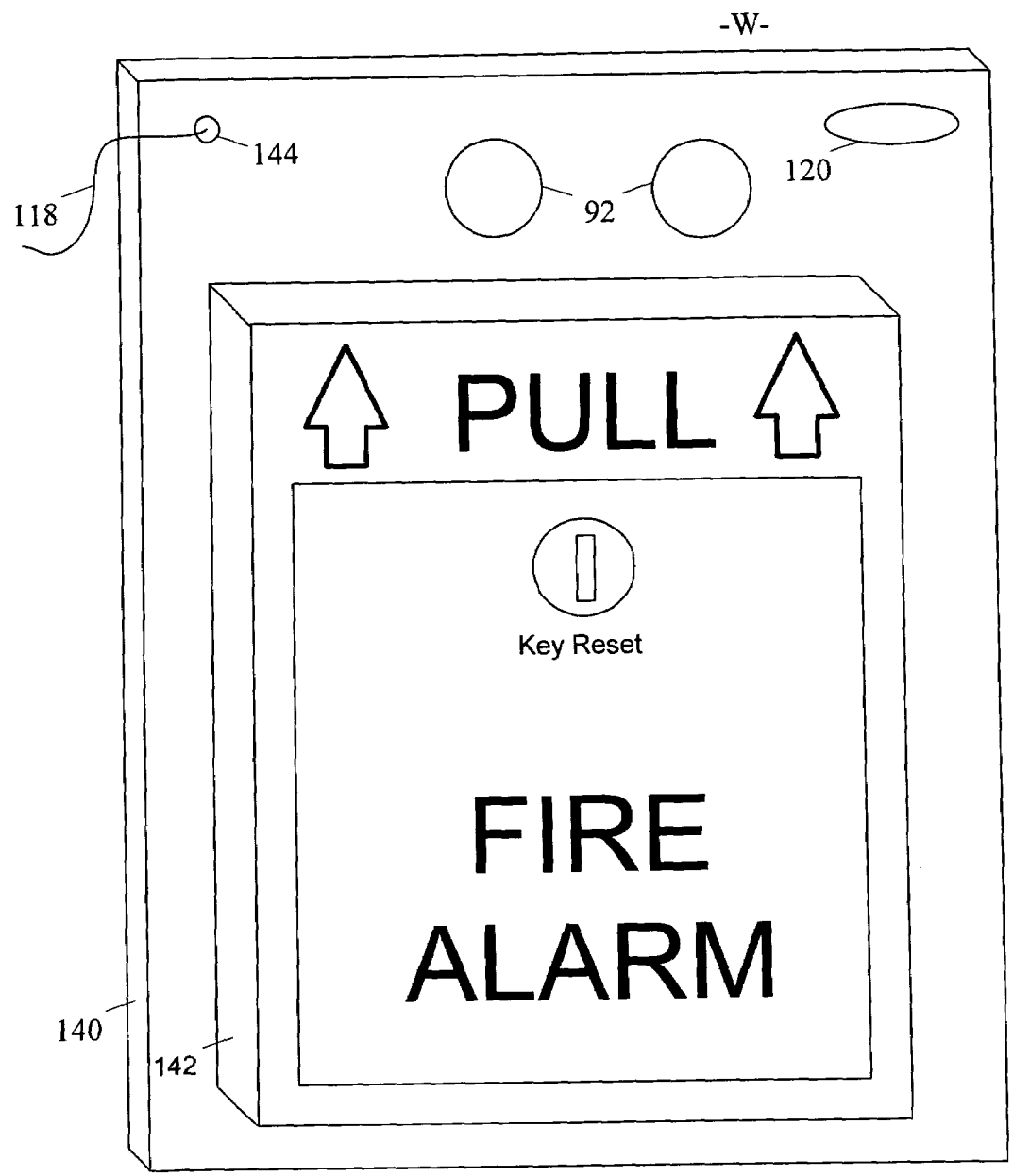
FIG. 6 is a perspective view of a fire alarm pull station for remote inspection according to the invention.

Along with remote inspection of one or a system of fire extinguisher stations, in another embodiment, the apparatus 10 of the invention is used for remote inspection of other emergency equipment installed at one or a system of emergency equipment stations. Referring to FIG. 6, in another embodiment, components of docking station 30, as described above, may instead be included in a housing 140 that is shown mounted to a wall, post, or other support surface, W, and receives a fire alarm pull station 142 such that the pull station is positioned on an appropriate location of the support surface, W, for reasonable access. By including the components of the docking station 30 in the housing 140, the fire alarm pull station 142 is capable of remote inspection similar to the fire extinguisher station 16. In the embodiment shown, housing 140 contains the sonar module 90 and defines the apertures or windows 92 for emitting and receiving ultrasonic signals to detect one or more objects that obstruct viewing of and access to the fire alarm pull station 142. Additionally, in some embodiments the housing 140 and the fire alarm pull station are in communication for signal transmission and reception. For example, if the fire alarm pull station 142 is pulled by a passerby in the event of an emergency to sound a fire alarm, a signal is issued by the pull station and passed to the housing 140 for transmission to the remote central station 26. The fire alarm pull station 142 may also initiate other signals based on other internal conditions associated within the pull station. For example, a signal may be initiated if a battery included in the fire alarm pull station 142 needs to be replaced or recharged.

Similar to the housing 30 (FIG. 2), the sonar module 90 included in the housing 140 initiates a signal to indicate an obstruction that may restrict visibility of or access to the fire alarm pull station 142. To initiate the signal, the electronic and communications circuitry 94 is also disposed within the housing 140 for transmitting the signal to the remote central station 26. To transmit the signal, the electronic and communications circuitry 94 sends the signal via a hardwire connection or a wireless link from the housing 140 to the remote central station 26. To provide a hardwire connection, in this embodiment the housing 140 includes a connection terminal 144 for connecting to the hardwire connection 118 for transmitting signals to and receiving signals from the remote central station 26. In other embodiments a wireless link is established between the housing 140 and the remote central station 26 for transmitting and receiving signals. For example, wireless communication circuitry and an antenna 120 are included within the housing 140 to communicate by wireless signal between the housing 140 and the previously mentioned RF monitoring system receiver, e.g., at the remote central station 26. Also, in some embodiments the antenna 120 and wireless communication circuitry is capable of receiving wireless signals from the remote central station 26, other wireless devices (e.g. cellular telephone, etc.), or from one or more other emergency equipment stations for relaying signals in a networking scheme. By forming a network (e.g., a local area network, wide area network, or similar) with hardwire connections or wireless links, or a combination of hardwire connections and wireless links, a system of fire alarm pull stations along with other emergency equipment stations (e.g., a fire extinguisher station 16), distributed over a considerable area, are capable of being inspected remotely by the remote central station 26. Additionally in some embodiments the housing 140 includes the electronic and communications circuitry 94 and wireless communication circuitry for providing redundant transmission pathways between the remote central station 26 and the housing 140 for providing a backup communication system.

Along with transmitting internal conditions (e.g., battery replacement or recharging, etc.) and external conditions (e.g., detection of an obstruction, etc.) associated with the fire alarm pull station 142, in some embodiments the housing 140 or the fire alarm pull station provide local indications that the pull station has been operated in the event of an emergency For example, the housing 140 can include or be in communication with an audible signaling device (e.g., a speaker) for emitting an audible tone or signal (e.g., verbal commands) to alert people in the local vicinity to a detected obstruction of the pull station or other external condition such as the operation of the pull station by a passerby due to a fire. The audible signal may also consist of a recorded information message, e.g., instructions for evacuation or for assisting personnel located near the fire alarm pull station 142. Also, the housing 140 may include one or more alert lights, strobes, or other similar lighting devices that are driven by circuitry included in the housing 140 such that the alert lights illuminate, flash, or strobe for visually alerting personnel in the vicinity that access to and view of the fire alarm pull station 142 is obstructed, or that the pull station has been actuated.

Figure 7:
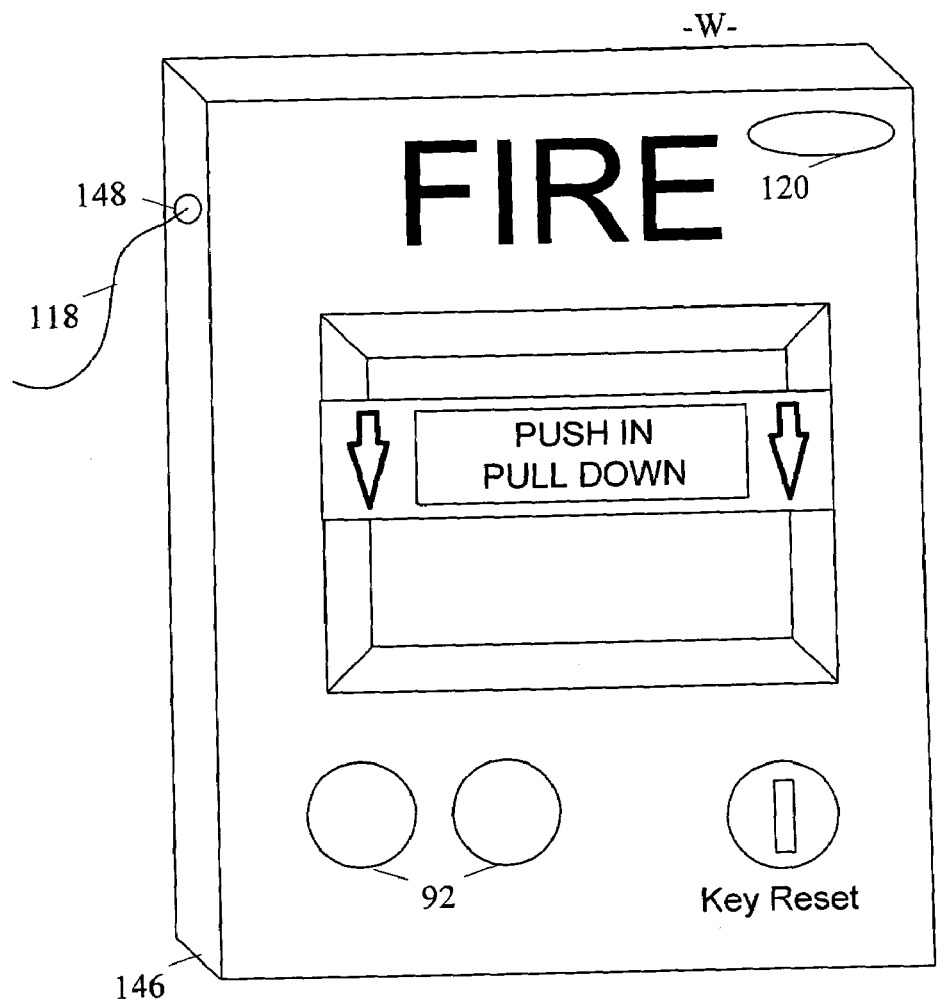
FIG. 7 is a perspective view of another embodiment of a fire alarm pull station for remote inspection according to the invention.

Referring to FIG. 7, in another embodiment, components of docking station 30, as described above, are included within a fire alarm pull station 146, rather than in a housing that receives the pull station as shown in FIG. 6. In the embodiment of FIG. 7, the fire alarm pull station 146 includes the sonar module 90 and defines the apertures or windows 92 for emitting and receiving ultrasonic signals for detecting obstructions a ranges e.g., from about 6 inches to about 10 feet dependent upon the environment as previously mentioned. By including the sonar module 90 along with the electronic and communication circuitry 94 within the fire alarm pull station 146, the pull station is capable of being located on a wall, post, or other support surface, W, that may provide a relatively smaller area for securing the pull station that may be ill-suited for supporting the larger housing 140 shown in FIG. 6.

Similar to the housing 140, by including the sonar module 90 in the fire alarm pull station 146, along with the apertures or windows 92, obstructions to the visibility and the accessibility of the pull station are detectable by the sonar module and a signal is issued by the electronic and communication circuitry 94 to the remote central station 26. Also similar to the housing 140, in this embodiment the fire alarm pull station 146 includes a connection terminal 148 for connecting the hardwire connection 118 to the pull station for transmitting signals to and receiving signals from the remote central station 26. Alternatively, or in concert with the hardwire connection 118, the fire alarm pull station 146 may include wireless communication circuitry and an antenna 120 (FIG. 1) to transmit and receive wireless signals to and from the previously mentioned RF monitoring system receiver, e.g., at the remote central station 26 and provide the capability to distribute a system of fire alarm pull stations over a considerable area while maintaining wireless communication between each fire alarm pull station and the remote central station 26. Additionally, in some embodiments the fire alarm pull station 146 includes an audible signaling device (e.g., a speaker) and/or alert lights for issuing an alert to nearby personnel or passersby that the pull station is. e.g., being obstructed.

Figure 8:
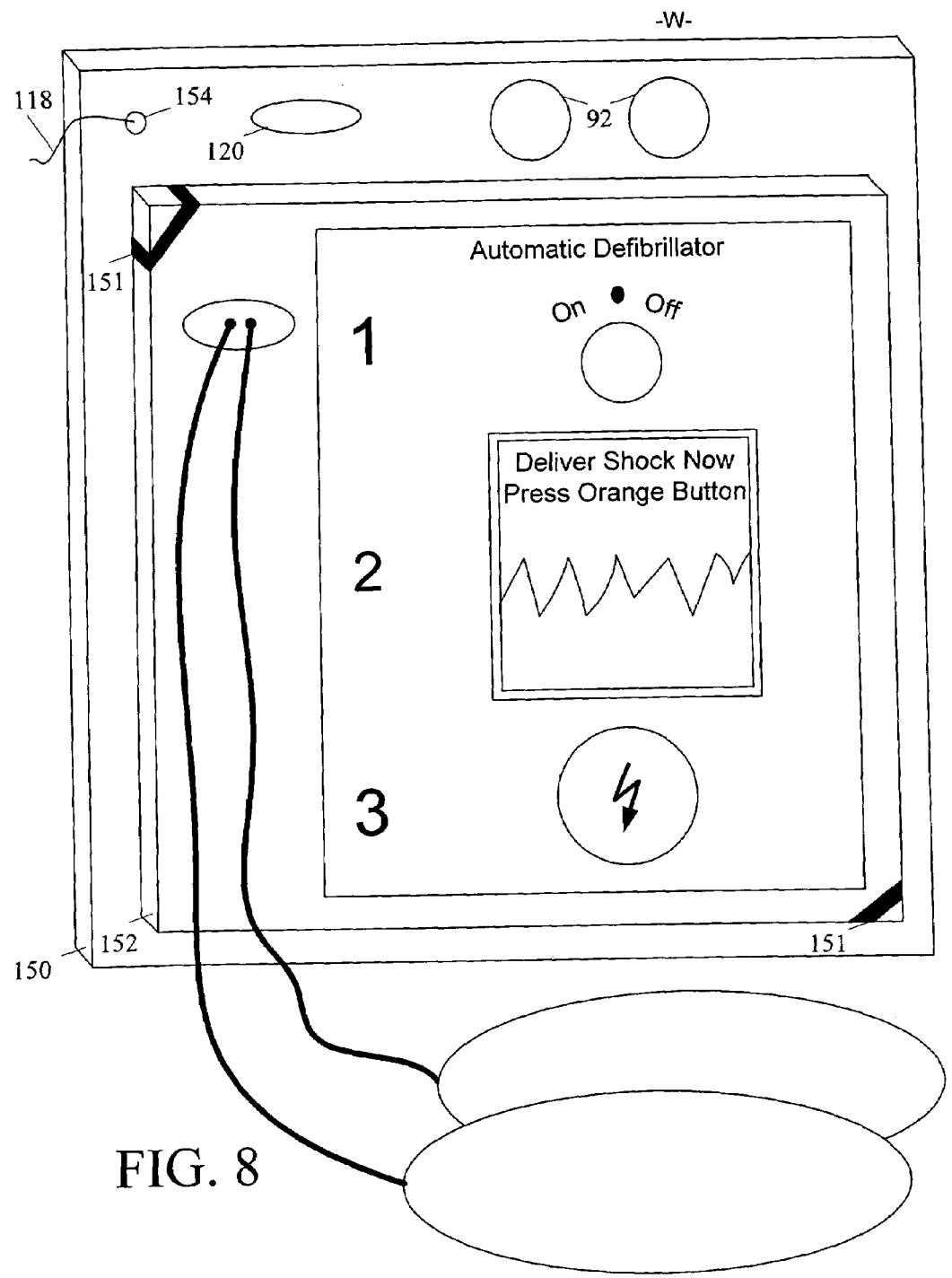
FIG. 8 is a perspective view of a defibrillator mounted at a defibrillator station for remote inspection according to the invention.

Referring to FIG. 8, in another embodiment, components of docking station 30, as described above, are included within a defibrillator station 150 that includes one or more mechanical fasteners 151 (e.g., a clips, fastening material, etc.) along with a recess for holding a defibrillator 152. Typically, the defibrillator station 150 is mounted to a wall, post, or other support surface, W, so that the defibrillator 152 is accessible by trained personnel or the general public for use during an emergency such as a person suffering from sudden cardiac arrest or other life-threatening aliment. By distributing a system of defibrillator stations, for example, throughout an airport, shopping center, or other facility accessible by the public, in the event of an emergency a defibrillator can be removed from a relatively nearby defibrillator station to provide assistance.

The defibrillator station 150 contains the electronic and communications circuitry 94 along with sonar module 90 and the apertures or windows 92 for emitting and receiving ultrasonic signals to detect obstructions as previously mentioned. By including the sonar module 90 within the defibrillator station 150, obstructions to the visibility and the accessibility of the defibrillator station are detectable and upon such detection a signal is issued by the electronic and communications circuitry 94 for transmitting to the remote central station 26 to provide an alert regarding the obstruction. In this embodiment the signal is transmitted from the electronic and communication circuitry 94 to a connection terminal 154 and then to a hardwire connection 118 that is in communication with the remote central station 26. Alternatively, the signal indicating the obstruction can be transmitted in a wireless signal to the remote central station 26 from an antenna 120 included on the defibrillator station. Additionally in some embodiments, similar to the fire extinguisher station 16 (shown in FIG. 2), a signal that indicates one or more internal conditions of the defibrillator 152 and/or the defibrillator station 150 are transmitted to the remote central station 26. For example, if the defibrillator 152 is removed from the defibrillator station 150 (e.g., in the event of an emergency), or if an internal battery needs attention (e.g., replacing, recharging, etc.), or if another similar or previously mentioned predetermined internal condition occurs, a signal is transmitted in a signal to the remote central station 26 over the hardwire connection 118 and/or in a wireless signal from the antenna 120.

Along with providing a signal to the remote central station 26 indicating internal and/or external conditions of the defibrillator 152 and/or the defibrillator station 150, in some embodiments the defibrillator station includes an audible signaling device (e.g., a speaker) that issues an audible tone, signal, or message for alerting personnel and/or the general public to one or more of the predetermined internal and external conditions. For example, if the defibrillator station 150 is obstructed, or if the defibrillator 152 is removed from the defibrillator station, an audible tone may be emitted by the audible signaling device. Also, the defibrillator station 150 may include one or more alert lights, strobes, or other similar lighting devices for similarly alerting personnel and/or the general public to the one or more of the predetermined internal or external conditions associated with the defibrillator station or the defibrillator 152.

Figure 9:
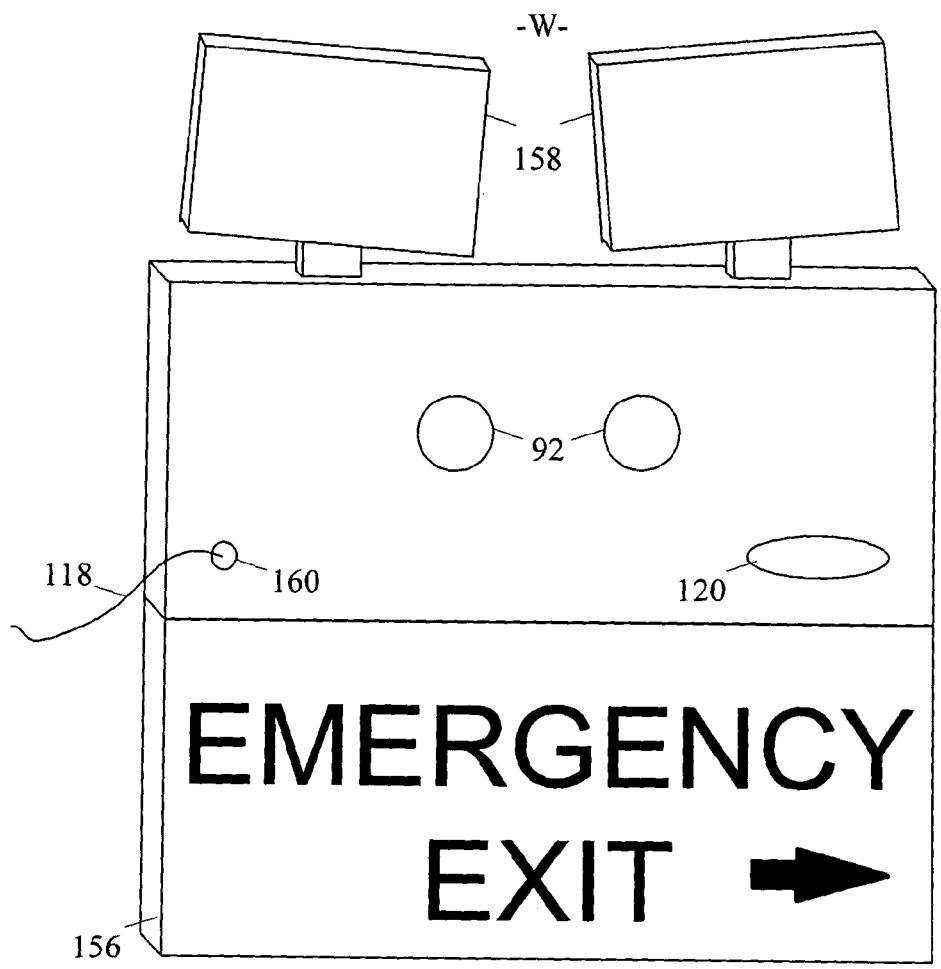
FIG. 9 is a perspective view of an emergency lighting station for remote inspection according to the invention.

Referring to FIG. 9, in another embodiment, components of docking station 30, as described above, are included in an emergency lighting station 156 that provides, e.g., a pair of emergency lights 158 that provide illumination in the event of an emergency (e.g., a fire, a power outage, etc.). In some embodiments, activation of the emergency lights 158 is controlled remotely, e.g., from the remote central station 26, or controlled locally by circuitry and sensors (e.g., a smoke detector) included in the emergency lighting station 156 or positioned in a nearby location (e.g., mounted in a ceiling). Typically, the emergency lighting station 156 is mounted to a wall, post, or other support surface (e.g., a ceiling, doorway, etc.), W, for illuminating the local area during an emergency. In some embodiments, a system of emergency lighting stations are distributed throughout a commercial, industrial, educational, or other similar type of facility to provide emergency lighting. Additionally, in this embodiment, the emergency lighting station 156 includes an "EMERGENCY EXIT" signal, which may or may not illuminate while directing people to an appropriate egress point (e.g., doorway) during an emergency.

Similar to previously mentioned embodiments, the emergency lighting station 156 contains the sonar module 90 and defines the apertures or windows 92 for detecting obstructions. By including the sonar module 90 within the emergency lighting station 156, obstructions to operation of the emergency lighting station, i.e. illumination of the area intended to be illuminated, are detectable by the sonar module and a signal is initiated from the electronic and communications circuitry 94 also included in the station. Similar to previously mentioned embodiments, the emergency lighting station 156 includes a connection terminal 160 that connects to the hardwire connection 118 for transmitting the signal to the remote central station 26. In some embodiments the emergency lighting station also includes wireless communication circuitry and the antenna 120 to provide wireless transmission of the signal to the previously mentioned RF monitoring system receiver, e.g., at the remote central station 26. Additionally, in some embodiments, the emergency lighting station 156 includes circuitry for transmitting both wireless signals over the antenna 120 and hard-wire signals over the hardwire connection 118 for redundancy to provide a back-up signal transmission pathway.

The signal sent from the emergency lighting station 156 alerts the remote central station 26 to one or more predetermined external conditions associated with the station such as an obstruction detected by the sonar module through the apertures or windows 92. The signal may also alert the remote central station 26 to predetermined internal conditions associated with the station 156 such as if a battery back-up needs replacing or recharging, or if one of the emergency lights 158 need to be replaced. Additionally, the emergency lighting station 156 may include an audible signaling device (e.g., a speaker) for emitting an audible tone, signal, or message to alert facility personnel and/or the general public in the vicinity that the station is currently obstructed or another predetermined internal or external condition has occurred. Also, the emergency lighting station 156 may include one or more alert lights, strobes, or other similar lighting devices, in addition to the emergency lights 158, for emitting a visual alert to indicate, e.g., the emergency lighting station is obstructed.

Figure 10:
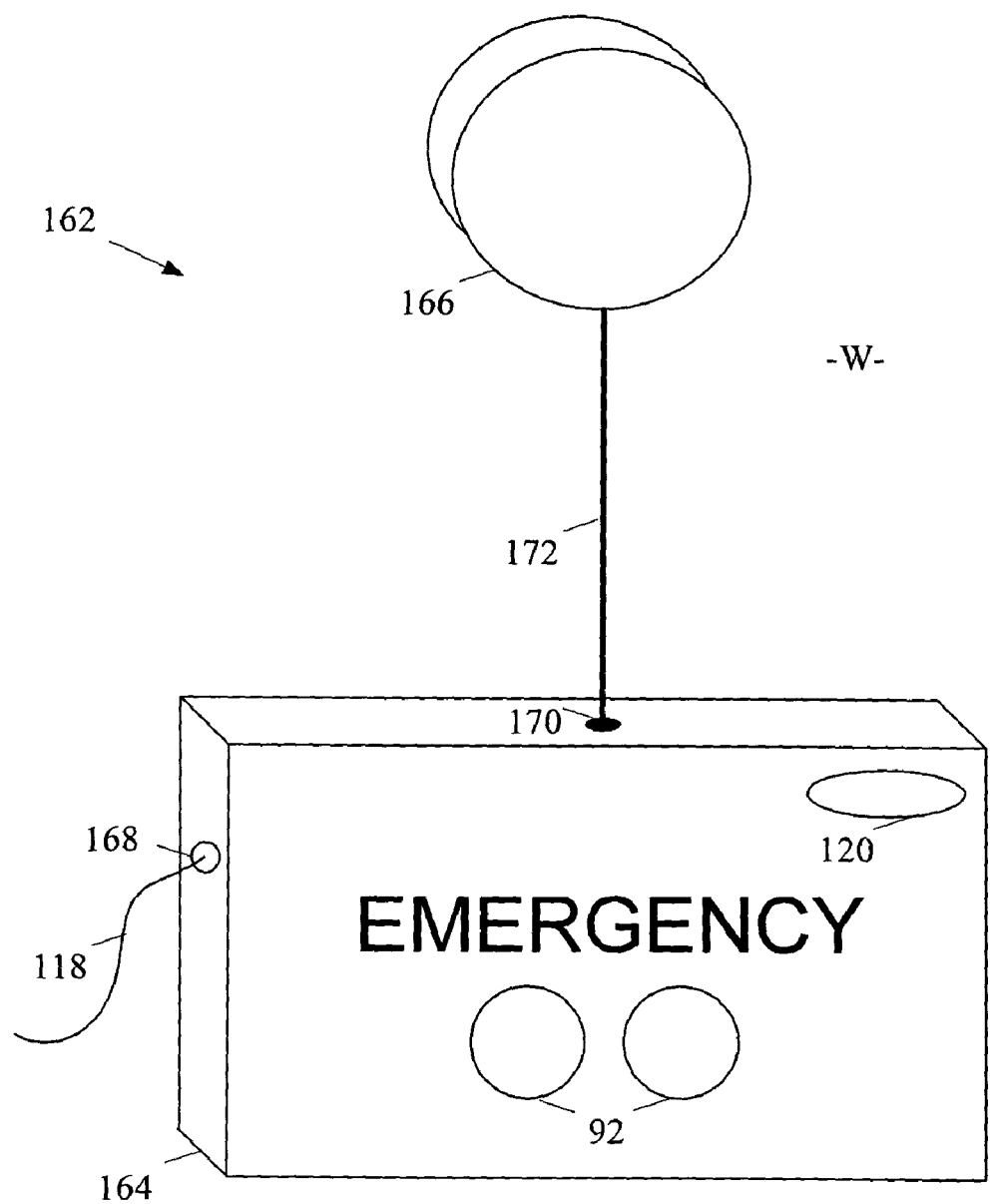
FIG. 10 is a perspective view of an emergency egress station for remote inspection according to the invention.

Referring to FIG. 10, in another embodiment, components of docking station 30, as described above, are included in an emergency egress station 162 that includes a housing 164 that is in communication with, e.g., a strobe 166 that provides illumination in the event of an emergency (e.g., a fire, a power outage, etc.). In some embodiments, activation of the strobe 166 is controlled remotely, e.g., from the remote central station 26, or controlled locally by circuitry and sensors (e.g., a smoke detector) included in the emergency egress station 162 or positioned in a nearby location (e.g., mounted in a ceiling). Typically, the emergency egress station 162 is mounted to a wall, post, or other support surface (e.g., a ceiling, doorway, etc.), W, for illuminating the local area during an emergency. Furthermore, in some embodiments the emergency egress station 162 is mounted on the support surface approximately slightly above floor level, such that a person crawling along the floor in the event of an emergency (e.g., fire) can detect the illuminating strobe to be directed to an appropriate egress point such as an emergency exit doorway.

Similar to previously mentioned embodiments, the housing 164 of the emergency egress station 162 contains the sonar module 90 and defines the apertures or windows 92 for detecting obstructions. By including the sonar module 90 within the housing 164, obstructions to operation of the emergency egress station 162, i.e. illumination of the area intended to be illuminated, are detectable by the sonar module and a signal is initiated from the electronic and communications circuitry 94 also included in the housing. Similar to previously mentioned embodiments, the housing 164 of the emergency egress station 162 includes a connection terminal 168 that connects to the hardwire connection 118 for transmitting the signal to the remote central station 26. In some embodiments the housing 164 also includes wireless communication circuitry and the antenna 120 to provide wireless transmission of the signal to the previously mentioned RF monitoring system receiver, e.g., at the remote central station 26. Additionally, in some embodiments, the housing 164 includes circuitry for transmitting both wireless signals over the antenna 120 and hardwire signals over the hardwire connection 118 for redundancy to provide a back-up signal transmission pathway.

The signal sent from the emergency egress station 162 alerts the remote central station 26 to one or more predetermined external conditions associated with the station such as an obstruction detected by the sonar module through the apertures or windows 92. The signal may also alert the remote central station 26 to predetermined internal conditions associated with the station 162 such as if a battery needs replacing or recharging, or if the strobe 166 needs to be replaced. Additionally, the emergency egress station 162 may include an audible signaling device (e.g., a speaker) for emitting an audible tone, signal, or message to alert facility personnel and/or the general public in the vicinity that the station is currently obstructed or another predetermined internal or external condition has occurred. Also, the emergency egress station 162 may include one or more additional strobes, or other similar lighting devices, for emitting a visual alert to indicate, e.g., the emergency egress station 162 is obstructed or in the event of an emergency as provided by a signal received on the hardwire connection 118 or the antenna 120.

In this particular embodiment the housing 164 includes a terminal 170 that connects a hardwire 172 between the housing 164 and the strobe 166 so that the strobe is activated by a signal from the housing. Alternatively, antenna 120, or another antenna included in the housing 164, can establish a wireless link between the housing and the strobe 166 such that a wireless signal transmitted from the housing activates the strobe. Also, in some embodiments, the strobe 166 is activated by a signal initiated by another signal received by the housing 164. For example, in some embodiments the housing 164 is in communication with emergency equipment such as a fire alarm pull station, a defibrillator, a smoke detector, or other emergency equipment that provides a signal to activate the strobe 166 in the event of an emergency.

Similar to the docking station 30 (shown in FIG. 2), in some embodiments, the housing 164 is fixedly mounted to the wall, W, with or without the strobe 166, at a predetermined position spaced from a fire extinguisher, a fire alarm pull station, a defibrillator, or other piece of emergency equipment. So, for example, rather than incorporating the components of docking station 30 (e.g., the sonar module, the apertures 92, the electronic and communications circuitry 94, etc.) into a housing that is positioned in close proximity to the emergency equipment, or incorporated into the emergency equipment, the components are incorporated into the housing 164 that is positioned a distance away from the equipment and communicates with the emergency equipment via the hardwire connection 118 or by a wireless link established with the antenna 120. By communicating with the emergency equipment in the event of an emergency (e.g., a fire alarm pull station is pulled) a signal is sent from the emergency equipment to the housing 164 to activate the strobe 166 or, for example, upon receiving the signal, the housing sends a signal over the hardwire connection 118 to the remote central station 26, or both.

Figure 11:
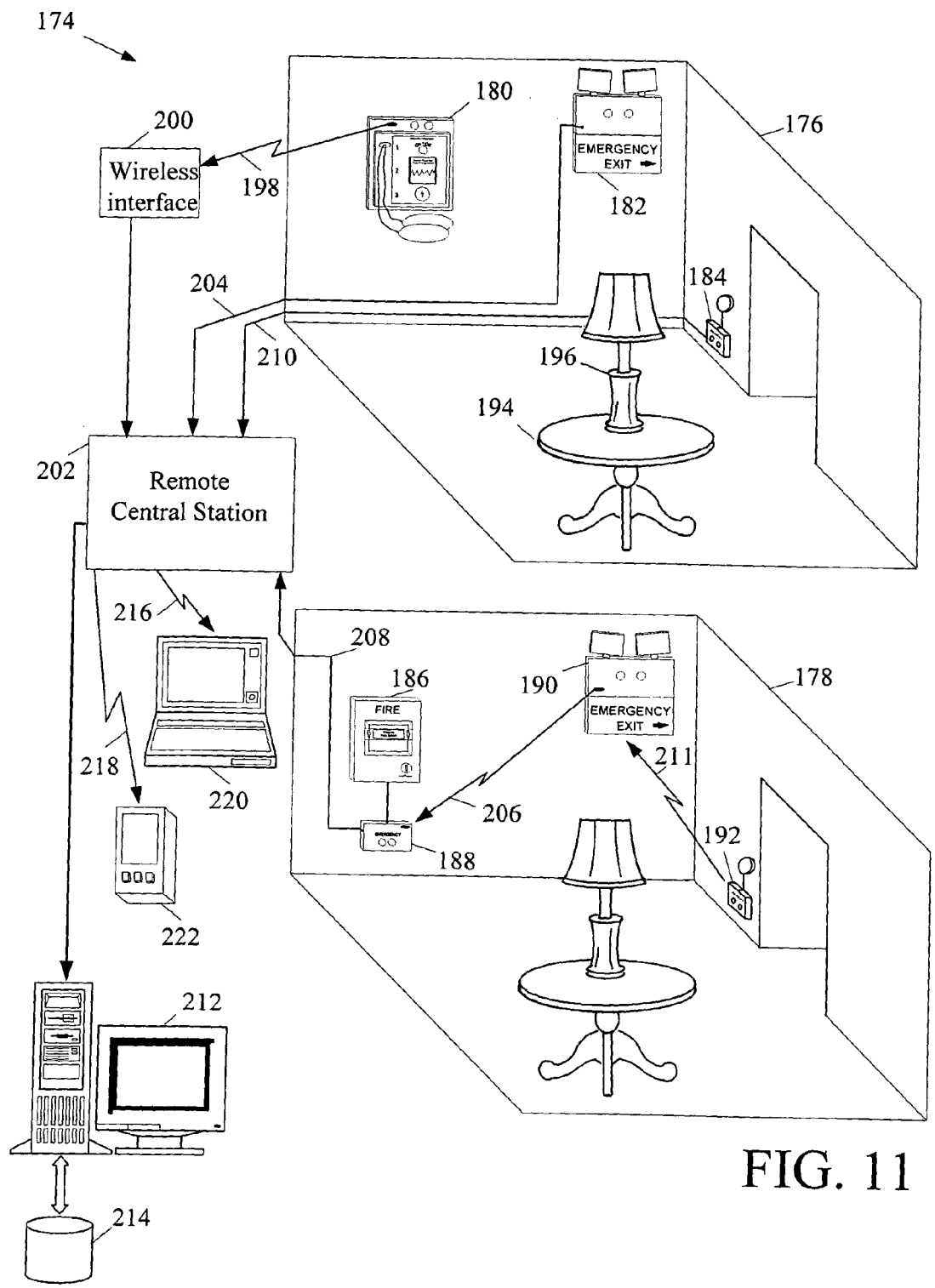
FIG. 11 is a somewhat diagrammatic view of an apparatus of the invention for remote inspection of emergency equipment stations distributed throughout a facility.

Referring to FIG. 11, in another embodiment, an apparatus 174 of the invention for remote inspection of emergency equipment includes means for monitoring the visibility and accessibility of emergency equipment stations distributed throughout locations (e.g., rooms, hallways, etc.) associated with a healthcare facility (e.g., a hospital, assisted living facility, a nursing home, etc.), a commercial facility (e.g., a shopping mall, restaurant, dance club, gymnasium, etc.), an educational institution (e.g., a college campus, dormitory, etc.), a residence (e.g., a residential home, residential development, apartment complex, condominium complex, etc.), or other facility (e.g., an airport, train station, bus station, etc.). In this particular example, emergency equipment stations are distributed throughout two rooms 176, 178 for assisting people in the event of an emergency. For example, room 176 includes a wall-mounted defibrillator station 180 that includes a detachable defibrillator for use during a life-threatening event such as a sudden cardiac arrest. Room 176 also includes an emergency lighting station 182 and an emergency egress station 184 that provides lighting to assist egress in the event of an emergency such as fire, a power outage, etc. Room 178 includes a fire alarm pull station 186 for initiating a signal to alert the appropriate personnel (e.g., a fire department, facility management, etc.) along with other people (e.g., the general public) to an emergency such as a fire. In this embodiment a housing 188 is in communication with the fire alarm pull station 186, and includes a sonar module and apertures rather than the pull station. Room 178 also includes an emergency lighting station 190 and an emergency egress station 192 for assisting egress from the room during times of emergency.

Each of the emergency equipment stations 180, 182, 190, 192, and the housing 188 includes a sonar module and apertures for detecting obstructions to the visibility or operation of, or access to, each respective station. For example if an object such as a table 194 and lamp 196 is placed in front of the defibrillator station 180, the obstruction is detected by the ultrasonic signals transmitted and received through apertures of the defibrillator station 180. For example, the ultrasonic signals may detect obstructions of about 6 inches to about 10 feet in front of the defibrillator station 180. Once an obstruction is detected, the defibrillator station 180, which includes wireless signal transmission and reception circuitry (e.g., an RF circuit, antenna, etc.), initiates and transmits a wireless signal 198 with the antenna included in the defibrillator station that is received by a wireless interface 200 that is in communication with a remote central station 202. The wireless signal 198 is used by the remote central station 202 to alert appropriate personnel (e.g., facility maintenance personnel) that the defibrillator station 180 is currently obstructed. Additionally, in this embodiment the wireless signal 198 is capable of communicating information associated with other predetermined external conditions (e.g., removal of the defibrillator from the defibrillator station) or predetermined internal conditions (e.g., needed replacement or recharging of a battery) associated with the defibrillator station 180.

Similar to the emergency lighting station 156 shown in FIG. 9, the emergency lighting stations 182 and 190 respectively include sonar modules for detecting obstructions to operation of or accessibility to the stations. Here, when an obstruction is detected by the emergency lighting station 182, a signal is transmitted through a hardwire connection 204 that is in communication with the remote central station 202. However, when emergency lighting station 190 detects an obstruction, a wireless signal 206 is transmitted to the housing 188 that includes circuitry for relaying the signal over a hardwire connection 208 to the remote central station 202. Additionally, the housing 188 includes circuitry for combining (e.g., multiplexing) the received signal 206 with one or more signals produced by the fire alarm pull station 186 for transmitting a combined signal on the hardwire connection 208 to the remote central station 202. Additionally, in this embodiment, the emergency egress station 184 transmits a signal though a hardwire connection 210 to the remote central station 202 when an obstruction is detected. Alternatively, the emergency egress station 192 transmits a wireless signal 211 for alerting the remote central station 202 to a detected obstruction. In this example, the wireless signal 211 is transmitted to the emergency lighting station 190, which includes circuitry for relaying the signal to the remote central station 202 via the housing 188. However, in some embodiments the wireless signal 211 is transmitted via another pathway. For example, the wireless signal is transmitted directly to the housing 188 for relaying over the hardwire connection 208 to the remote central station 202.

In some embodiments the defibrillator station 180 and/or the emergency lighting stations 182, 190 and/or the emergency egress station 184, 192 also include circuitry for relaying and/or combining (e.g., multiplexing) signals so that a network (e.g., a local area network, LAN, or a wide area network, WAN, etc.) is formed for passing signals among the emergency equipment stations. Additionally, to form a network among the emergency equipment stations, circuitry (e.g., read-only memory, random access memory, etc.) or another a type of memory storage devices (e.g., an radio frequency (RF) tag) are included in each emergency equipment station for storing unique identification information that can be encoded in transmitted signals, thereby permitting the remote central station 202 to differentiate among the emergency equipment stations as to the source of the transmitted signal. By identifying the transmission source, facility personnel located at the remote central station 202 are alerted to the particular emergency equipment station associated with internal conditions (e.g., battery replacement needed) and/or external conditions (e.g., obstruction) indicated by in the received signal.

In some embodiments, with reference to the defibrillator station 180 in room 176, the wireless interface 200 may receive the wireless signal 198 directly from the defibrillator station 180 (e.g. via line of site transmission, etc.). However the wireless signal may also be relayed across additional wireless links (e.g., cellular links, satellite links, etc.) prior to being received at the wireless interface 200. Also, in some embodiments, a combination of wireless links and hardwire connections can be used to transmit the signals from the defibrillator station 180 or any of the emergency equipment stations or the remote central station 202.

After signals are received at the remote central station 202 from the rooms 176, 178, the information included in the received signals is sorted and displayed by a computer system 212 to alert facility personnel (e.g., security, maintenance, fire department, etc.) as to the internal and external conditions associated with the emergency equipment stations. The computer system 212 also stores the received and sorted information on a storage device 214 (e.g., a hard drive, CD-ROM, etc.) for retrieval at a future time for further processing and reporting. In some embodiments, the remote central station 202 may include wireless transmission and reception circuitry for transmitting and receiving wireless signals. For example, wireless circuitry (e.g., RF circuitry, antenna, etc.) included in the remote central station 202 can be used to transmit information over wireless links 216, 218 to wireless devices such as a laptop computer 220, a personal digital assistant (PDA) 222, or other similar wireless devices (e.g., a cellular phone). Transmission of the information to wireless devices provides facility personnel not located at the remote central station 202 with information regarding the status of the emergency equipment stations and an alert to any problems (e.g., the fire alarm pull station 186 in room 178 is being obstructed as detected by housing 188) associated with one or more of the emergency equipment stations. By providing wireless access to the information collected at the remote central station 202, the response time of facility personnel to one or more of emergency equipment stations can be reduced.

Briefly, in summary, in a preferred embodiment, the means for detecting an obstruction to viewing (or operation) of or access to an emergency equipment station (e.g., a fire extinguisher station, a fire alarm pull station, a defibrillator station, an emergency lighting station, etc.) includes a sonar module 90 mounted within (e.g., FIG. 7), or mounted in connection to (e.g., FIG. 10), the emergency equipment station. The sonar module 90 periodically emits an ultrasonic signal through an aperture or window and detects when the signal is returned (reflected) by an obstruction within a predetermined region or range, e.g., from about 6 inches to about 10 feet from the emergency equipment station. Upon detection of an obstruction, a signal is issued to the remote central station 26 to indicate the presence of an obstruction as required by NFPA 10, §4-3.2(b). Remote inspection information included in the signal received by the remote central station 26 is communicated to means 28, e.g., a computer 106 (FIG. 1) located at the remote central station 26, or other location, where the information is compiled and stored for display and/or print-out in the form of periodic inspection report, e.g., to trigger corrective action. The remote central station 26 may also send signals 122 to the emergency equipment stations (e.g., fire extinguisher stations 16) to periodically check for these, and/ or other, predetermined internal and external conditions. The remote inspection apparatus 10 of the invention thus provides protection that meets or exceeds the requirements of NFPA 10, §4-3.2. Surveillance can be provided 24 hours per day, if desired.

In the preferred embodiment, a non-contact ultrasonic sensor (sonar module 90) is employed for detecting the presence of an obstruction. Alternatively, a non-contact optical sensor may be employed that has advantages similar to those of the ultrasonic sensor, i.e., low cost and simplicity. Both have sensitivity over wide ranges of distances (e.g., about 6 inches to about 10 feet, or other ranges as may be dictated, e.g., by environmental conditions). As an obstruction may move slowly, or may be relatively stationary, it may not be necessary to have the sensor active at all times; periodic sampling, e.g., once per hour, may be sufficient. On the other hand, the sonar module 90 included, for example in the fire alarm pull station 140 (FIG. 6) may also be utilized as a proximity or motion sensor, e.g., in a security system, e.g., to issue a signal to a remote central station 26 and/or to sound an alarm when movement is detected in the vicinity of the fire alarm pull station 140 while a building is secured, e.g., after business hours or during weekends or vacations. In this case, continuous operation may be dictated, at least during periods when the security system is active. Other features and characteristics that may be optimally employed, as desired, include: wide angle and narrow angle sensitivity, digital output (Is there an obstruction or not?), and/or analog output (e.g., How large an obstruction? and How far away from the docking station?).

A number of embodiments of the invention have been described. Nevertheless, it will be understood that various modifications may be made without departing from the spirit and scope of the invention. For example, other features that might be provided in connection with a remote inspection apparatus of the invention may include, in some instances: an electronic circuit that drives one or more lights included in a emergency equipment station for providing a visual alert to passerby that the visibility or accessibility of the station has been obstructed. Another circuit may optionally drive an audible signaling device (e.g., a speaker) included in the emergency equipment station to for emitting an audible tone or signal (e.g., verbal commands) instead of or in addition to the visual signal to provide an alert that an obstruction to the emergency equipment station has been detected. The audio signal may consist of a recorded information message, e.g., instructions for use of the fire extinguisher including the type of fire for which use is appropriate, e.g., paper, electrical, liquid, all types. The electronic circuit may also include a battery condition sensor to actuate a visual and/or audio signal, e.g., at the remote central station, when a low battery condition is detected The electronic circuit may also include a sensor adapted to sense other local conditions, e.g., smoke or fire, to actuate illumination of a light and/or audio signal device when smoke or other indications of a fire are sensed, e.g., to signal the location of the emergency equipment station, when visibility is low. The electronic circuit may include a timer set to actuate the visual and/or the audio signal after a predetermined period of time, e.g., the recommended period between inspections, unless the timer is reset. The electronic circuit may be responsive to a signal from an external source, e.g., a system of smoke detectors, another fire extinguisher or fire extinguisher station, a suppression system, or the like, to actuate the visual and/or the audio signal. The electronic circuit may also include an encoded identification specific to each emergency equipment station for identifying the station, to the remote central station and/or to other elements of a home or facility security system. Typically to identify the emergency equipment station the identification information is encoded into one or more of signals or messages transmitted to the remote central station through a hardwire connection or wireless link via communication circuitry (e.g., RF circuitry and an antenna) included in the emergency equipment station.

In other embodiments, two or more sonar modules 90 may be employed in for example, the fire alarm pull station 140 (FIG. 6), to provide additional beam coverage. Also, various technologies may be implemented to communicate by wireless signal among the fire alarm pull station and/or other emergency equipment stations (e.g., a defibrillator station) and/or the remote central station 26. Along with radio frequency (RF) signaling, infrared (IR) signaling, optical signaling, or other similar technologies may provide communication links. RF signaling, IR signaling, optical signaling, or other similar signaling technologies may also be implemented individually or in any suitable combination to communicate by wireless signal among the fire alarm pull station 12, the emergency equipment stations (e.g., the defibrillator station), and the remote central station 26.

In other embodiments, wireless signaling technology may incorporate telecommunication schemes (e.g., Bluetooth or similar) to provide point-to-point or multi-point communication connections among e.g., the fire alarm pull station and/or other emergency equipment stations (e.g., a defibrillator station) and/or the remote central stations 26. These telecommunication schemes may be achieved, for example, with local wireless technology, cellular technology, and/or satellite technology. The wireless signaling technology may further incorporate spread spectrum techniques (e.g., frequency hopping) to allow the extinguishers to communicate in areas containing electromagnetic interference. The wireless signaling may also incorporate identification encoding along with encryption/decryption techniques and verification techniques to provide secure data transfers among the devices.

In other embodiments, the fire alarm pull station and/or other emergency equipment stations (e.g., a defibrillator station) and/or the remote central station 26 may include or otherwise be associated with a Global Positioning System (GPS). The GPS may be used to determine, for example, the geographic location of each fire alarm pull station and provide location coordinates, via the wireless signaling technology, to the other emergency equipment stations (e.g., the defibrillator station) and/or the remote central stations. Thus, the GPS system may provide the location of the fire alarm pull stations and allow, for example, tracking of the frequency that fire alarm pull stations located in a particular region of a facility are obstructed.

In still other embodiments, various sensing techniques, besides the sonar modules 90, may be employed to sense objects obstructing access to and/or view (or operation) of the emergency equipment stations. Passive or active acoustic sensors may be implemented to detect obstructing objects. In other examples, obstructions may be sensed with electromagnetic sensing techniques (e.g., radar, magnetic field sensors), infrared (IR) sensing techniques (e.g., heat sensors, IR sensors), visual sensing techniques (e.g., photo-electric sensors), and/or laser sensing techniques (e.g., LIDAR sensors). These technologies may, for example, be utilized individually or in concert to sense obstructions that block access to and view of the fire alarm pull station.

Also, the signaling may use networking techniques to provide one-directional and/or multi-directional communications among the devices. In one example, signals from emergency equipment stations may be networked asynchronously, such as in an asynchronous transfer mode (ATM). The signals may also be networked synchronously, such as, for example, in a synchronous optical network (SONET). In still another example, the signals may be transmitted over a landline in an integrated services digital network (ISDN), as well as over other similar media, for example, in a broadband ISDN (BISDN).

A remote inspection apparatus of the invention may also be employed for remote inspection of multiple facilities that each include multiple or a system of emergency equipment stations. Communication between the emergency equipment stations and the remote central station, including hard-wire and wireless communication, may be carried on directly, or indirectly, e.g. via relaying devices, including other emergency equipment stations.

Accordingly, other embodiments are within the scope of the following claims.

What is claimed is:

1. Apparatus for remote inspection of emergency equipment in installed positions at one or a system of emergency equipment stations, said apparatus comprising:
   a detector located at a first emergency equipment station for detection of the presence of an obstruction to viewing of or access to the first emergency equipment station, wherein the detector includes a sonar module;
   a defibrillator station with a portable defibrillator located at the first emergency equipment station;
   a fire extinguisher station with a portable fire extinguisher located at the first emergency equipment station, wherein the portable fire extinguisher includes a fire extinguisher gauge for detecting and displaying pressure conditions of fire extinguishing material contained within a volume of a tank included in the portable fire extinguisher; and
   an electronic circuit in communication between the detector and a remote central station for issue of a signal to the remote central station upon detection of one or more selectable predetermined conditions including predetermined internal conditions and predetermined external conditions, wherein the predetermined external conditions include removal of the portable fire extinguisher, and wherein the communication between the detector and the remote central station includes a second emergency equipment station in the system of emergency equipment stations configured to pass signals between at least the first emergency equipment station and the remote central station.

2. The apparatus for remote inspection of claim 1, wherein the detector initiates a signal from the electronic circuit to the remote central station upon detection of the obstruction.

3. The apparatus for remote inspection of claim 2, wherein the signal includes a wireless signal.

4. The apparatus of remote inspection of claim 1, wherein the obstruction is disposed within a range of about 6 inches to about 10 feet from the first emergency equipment station.

5. The apparatus for remote inspection of claim 1, wherein the detector initiates a signal from the electronic circuit to another emergency equipment station upon detection of the obstruction.

6. The apparatus for remote inspection of claim 5, wherein the signal includes a wireless signal.

7. The apparatus for remote inspection of claim 1, wherein the electronic circuit is further adapted to issue a signal to the remote central station and to receive another signal from the remote central station.

8. The apparatus for remote inspection of claim 7, wherein the issued signal includes a wireless signal.

9. The apparatus for remote inspection of claim 1, wherein the electronic circuit further comprises a wireless signal transmitter for transmitting a wireless signal to the remote central station.

10. The apparatus for remote inspection of claim 1, wherein the electronic circuit further comprises a wireless signal receiver for receiving a wireless signal from the remote central station.

11. The apparatus for remote inspection of claim 1, wherein the electronic circuit further comprises a receiver for receiving a signal from another emergency equipment station.

12. The apparatus for remote inspection of claim 1, wherein the electronic circuit further comprises a receiver for receiving a wireless signal from another emergency equipment station.

13. The apparatus for remote inspection of claim 1, wherein the electronic circuit further comprises a transmitter for transmitting a signal to another emergency equipment station.

14. The apparatus for remote inspection of claim 1, wherein the electronic circuit further comprises a transmitter for transmitting a wireless signal to another emergency equipment station.

15. The apparatus for remote inspection of claim 1, wherein the detector is included in a housing separated from the emergency equipment.

16. A first emergency equipment station comprising:
a portable defibrillator;
a portable fire extinguisher, wherein the portable fire extinguisher includes a fire extinguisher gauge for detecting and displaying pressure conditions of fire extinguishing material contained within a volume of a tank included in the portable fire extinguisher;
a detector for detection of access to a removal of the defibrillator or portable fire extinguisher from an installed position;
a detector for detection of the presence of an obstruction to viewing of or access to the portable defibrillator or portable fire extinguisher, wherein the detector includes a sonar module; and
circuitry for transmitting a signal to a remote station upon detection of one or more selectable predetermined conditions including predetermined internal conditions and predetermined external conditions, wherein the predetermined external conditions include removal of the portable fire extinguisher, and wherein a communication between the detector and the remote station includes a second emergency equipment station in a system of emergency equipment stations configured to pass signals between at least the first emergency equipment station and the remote station.

17. The first emergency equipment station of claim 16 wherein the circuitry is configured to transmit a signal to the remote station upon detection of the presence of an obstruction to viewing of or access to the portable defibrillator.

18. The first emergency equipment station of claim 16 wherein the circuitry for transmitting a signal to a remote station comprises:
a wireless transmitter for transmitting a wireless signal to a remote station upon detection of removal of the defibrillator from its installed position.

19. The first emergency equipment station of claim 16 wherein the circuitry for transmitting a signal to a remote station is configured to interface with a hardwire connection that is in communication with the remote station.

20. The first emergency equipment station of claim 16 further comprising:
one or more batteries for supplying power to the portable defibrillator; and a detector for detecting a low battery condition of one or more of the batteries.

21. The first emergency equipment station of claim 20 wherein the circuitry is configured to transmit a signal to the remote station upon detection of the presence of an obstruction to viewing of or access to the portable defibrillator.

22. The first emergency equipment station of claim 16 wherein the detector for detection of access to the defibrillator comprises a detector for detecting removal of the defibrillator from the installed position.

23. The first emergency equipment station of claim 16 wherein the circuitry is further configured to produce an alarm at the emergency equipment station upon detection of access to the defibrillator at its installed position.

24. The first emergency equipment station of claim 23 wherein the alarm comprises an audible alarm.

25. The first emergency equipment station of claim 23 wherein the alarm comprises a visual alarm.

26. A first emergency equipment station comprising:
a portable defibrillator;
a portable fire extinguisher, wherein the portable fire extinguisher includes a fire extinguisher gauge for detecting and displaying pressure conditions of fire extinguishing material contained within a volume of a tank included in the portable fire extinguisher;
one or more batteries that supply power to the portable defibrillator or portable fire extinguisher;
a detector for detection of a low battery condition of one or more of the batteries;
a detector for detection of the presence of an obstruction to viewing of or access to the portable defibrillator or portable fire extinguisher, wherein the detector includes a sonar module; and
circuitry for transmitting a signal to a remote station upon detection of one or more selectable predetermined conditions including predetermined internal conditions and predetermined external conditions, wherein the predetermined external conditions include removal of the portable fire extinguisher, and wherein a communication between the detector and the remote station includes a second emergency equipment station in a system of emergency equipment stations configured to pass signals between at least the first emergency equipment station and the remote station.

27. The first emergency equipment station of claim 26 wherein the circuitry for transmitting a signal to a remote station comprises:
a wireless transmitter for transmitting a wireless signal to a remote station upon detection of removal of the defibrillator from its installed position.

28. The first emergency equipment station of claim 26 wherein the circuitry for transmitting a signal to a remote station is configured to interface with a hardwire connection that is in communication with the remote station.

29. The first emergency equipment station of claim 26 wherein the circuitry is configured to transmit a signal to the remote station upon detection of the presence of an obstruction to viewing of or access to the portable defibrillator.

* * * * *